US012674173B2

(12) United States Patent
Strano et al.

(10) Patent No.: US 12,674,173 B2
(45) Date of Patent: Jul. 7, 2026

(54) ORGANELLE-SELECTIVE GENE DELIVERY AND EXPRESSION IN THE CHLOROPLAST IN PLANTA USING CHITOSAN-COMPLEXED SINGLE-WALLED CARBON NANOTUBE CARRIERS

(71) Applicant: MASSACHUSETTS INSTITUTE OF TECHNOLOGY, Cambridge, MA (US)

(72) Inventors: Michael Strano, Lexington, MA (US); Seonyeong Kwak, Cambridge, MA (US); Tedrick Salim Lew, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 538 days.

(21) Appl. No.: 17/288,764

(22) PCT Filed: Nov. 12, 2019

(86) PCT No.: PCT/US2019/060874
§ 371 (c)(1),
(2) Date: Apr. 26, 2021

(87) PCT Pub. No.: WO2020/102166
PCT Pub. Date: May 22, 2020

(65) Prior Publication Data
US 2021/0395759 A1 Dec. 23, 2021

Related U.S. Application Data

(60) Provisional application No. 62/758,803, filed on Nov. 12, 2018.

(51) Int. Cl.
*C12N 15/82* (2006.01)

(52) U.S. Cl.
CPC ............................... *C12N 15/8206* (2013.01)

(58) Field of Classification Search
None
See application file for complete search history.

(56) References Cited

U.S. PATENT DOCUMENTS 8,536,324 B2 * 9/2013 Mohapatra et al. . A61K 9/0092
977/750
2012/0207795 A1 8/2012 Zink et al.

FOREIGN PATENT DOCUMENTS

WO 2013/138930 A1 9/2013

OTHER PUBLICATIONS

Demirer et al. (Aug. 22, 2017 bioRxiv DOI:10.1101/179549 20 total pages "Nanoparticle-Guided Biomolecule Delivery for Transgene Expression and Gene Silencing in Mature Plants"; of record IDS Apr. 26, 2021) (Year: 2017).*

(Continued)

*Primary Examiner* — Matthew R Keogh
*Assistant Examiner* — Rebecca Stephens
(74) *Attorney, Agent, or Firm* — McDonnell Boehnen Hulbert & Berghoff LLP

(57) ABSTRACT

In one aspect, a composition can include an organelle, and a nanoparticle having a zeta potential of less than −10 mV or greater than 10 mV contained within the organelle. In a preferred embodiment, the organelle can be a chloroplast and the nanoparticle can be a single-walled carbon nanotube associated with a strongly anionic or strongly cationic polymer.

13 Claims, 23 Drawing Sheets

(56)         References Cited

OTHER PUBLICATIONS

Mao et al. 2010 Advanced Drug Delivery Reviews 62:12-27 "Chitosan-based formulations for delivery of DNA and siRNA". (Year: 2010).*

English language translation of RU2663347C1 (published Aug. 3, 2018), retrieved via Espacenet (13 total pages excluding drawings pages). (Year: 2018).*

Zhang et al. (2007 Biotechnol. Appl. Biochem. 46:197-204 "A novel PEGylation of chitosan nanoparticles for gene delivery") (Year: 2007).*

Wong et al. 2016 Nano. Lett. 16:1161-1172 "Lipid Exchange Envelope Penetration (LEEP) of Nanoparticles for Plant Engineering: A Universal Localization Mechanism". (Year: 2016).*

Giraldo et al. "Plant nanobionics approach to augment photosynthesis and biochemical sensing" 2014 Nature Materials 13:400-408. (Year: 2014).*

Wong et al. "Lipid Exchange Envelope Penetration (LEEP) of Nanoparticles for Plant Engineering: A Universal Localization Mechanism" 2016 Nano Letters 16:1161-1172. (Year: 2016).*

Salim Lew et al. "Rational Design Principles for the Transport and Subcellular Distribution of Nanomaterials into Plant Protoplasts" 2018 Small 14:1802086(13 total pages). (Year: 2018).*

Demirer, GS et al. "Nanoparticle-Guided Biomolecule Delivery for Transgene Expression and Gene Silencing in Mature Plants". BioRxiv. Aug. 22, 2017; pp. 1-20; abstract; p. 3, paragraph 3; p. 5; paragraph 2; p. 6, paragraph 1; p. 9, paragraph 1; DOI: 10.1101/179549.

Nitta, SK et al. Biopolymer-Based Nanoparticles for Drug/Gene Delivery and Tissue Engineering, International Journal of Molecular Sciences. Jan. 14, 2013; vol. 14, No. 1; pp. 1629-1654; p. 1634, paragraph 2; DOI: 10.3390/ijms140411629.

International Search Report Issued on Feb. 3, 2020 in corresponding International Patent Application No. PCT/US2019/060874.

Written Opinion of the International Searching Authority Issued on Feb. 3, 2020 in corresponding International Patent Application No. PCT/US2019/060874.

* cited by examiner

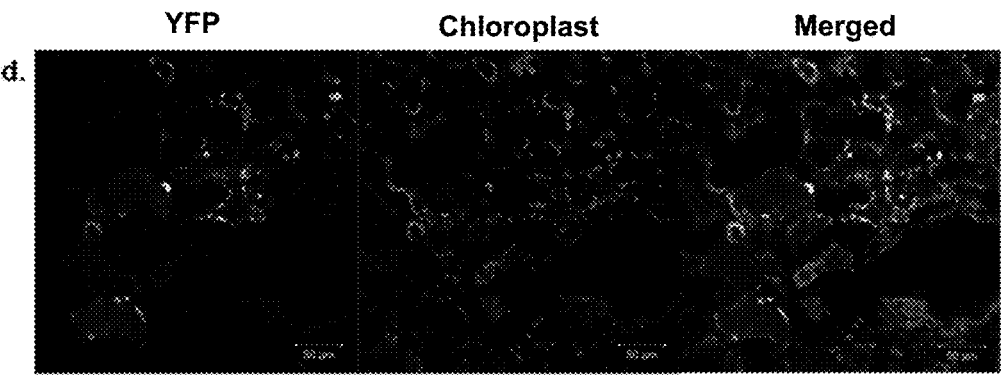
Figure 4D
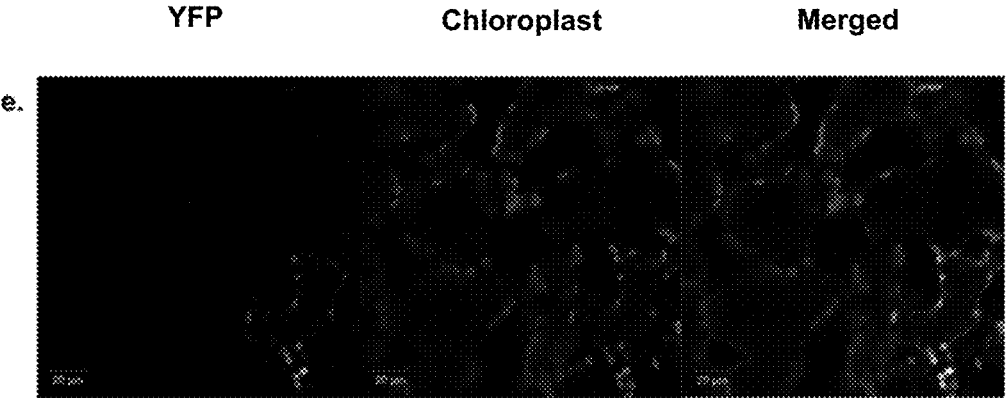
Figure 4E
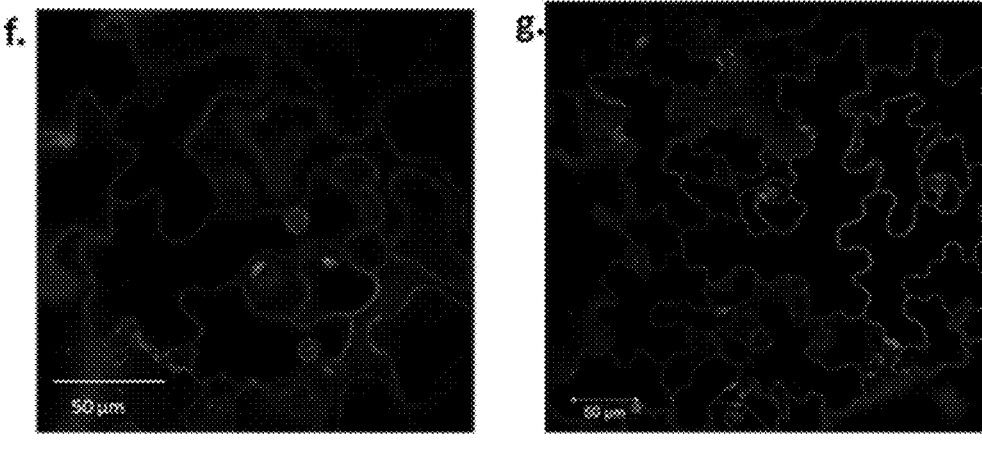
Figure 4F                                    Figure 4G YFP                Chloroplast            Merged YFP                Chloroplast            Merged

C.

D.

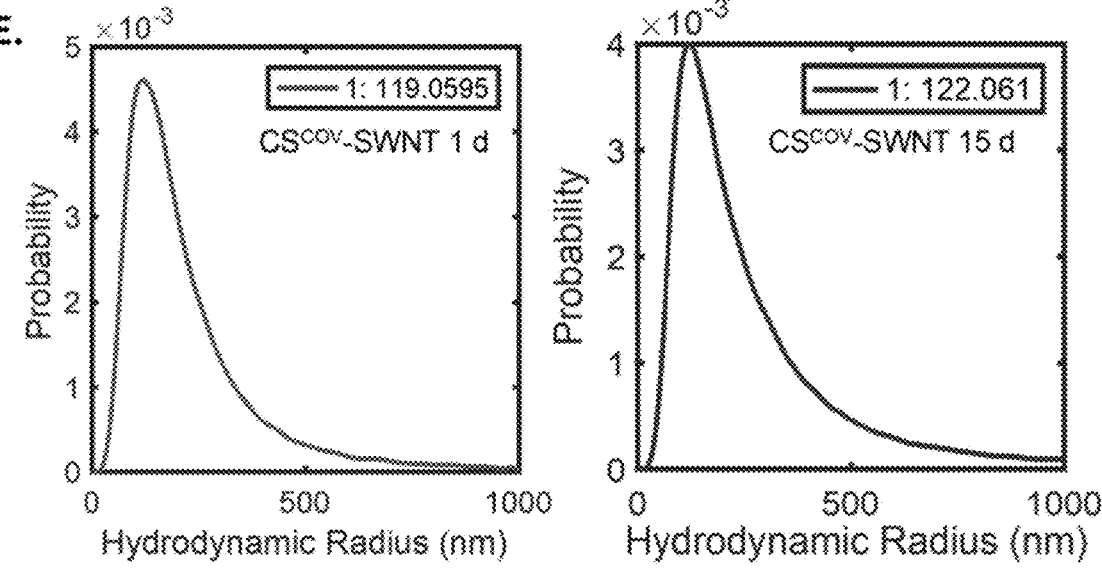
Figure 7E
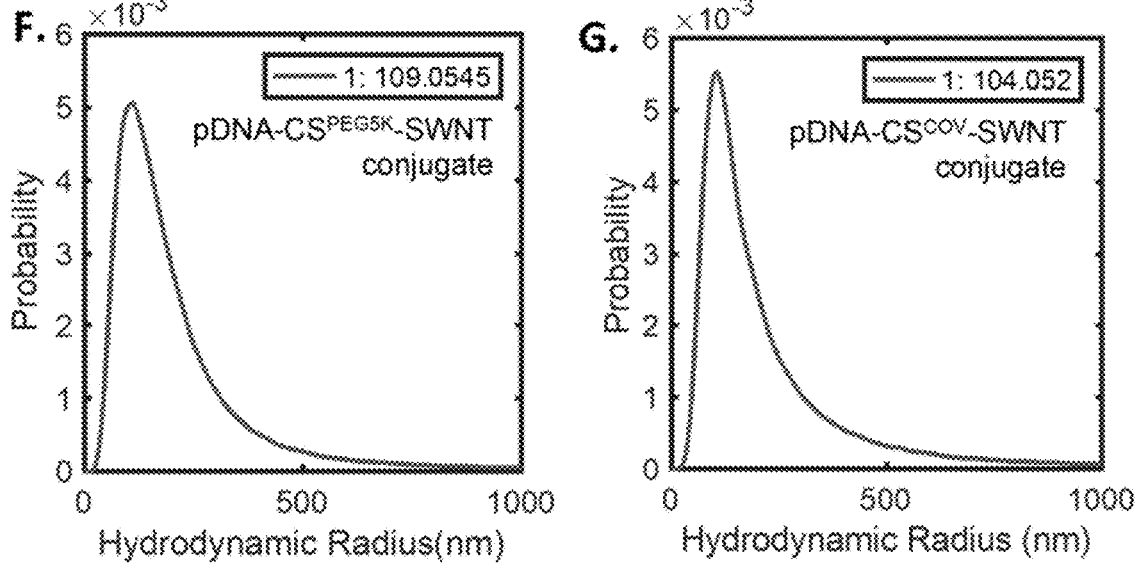
Figure 7F                                              Figure 7G

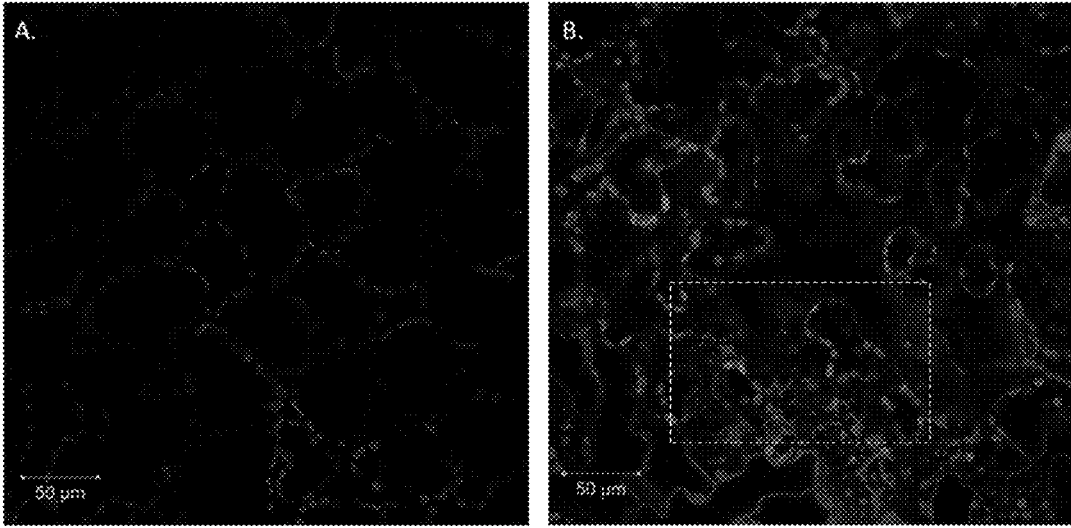
Figure 8A                                    Figure 8B
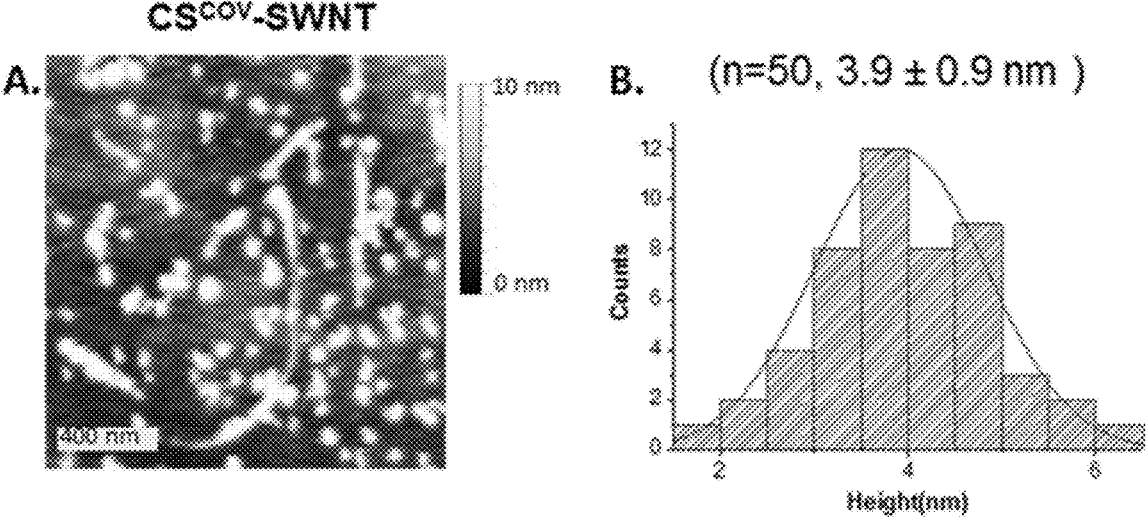
Figure 9A                                    Figure 9B pDNA:CS$^{COV}$-SWNT = 1:1
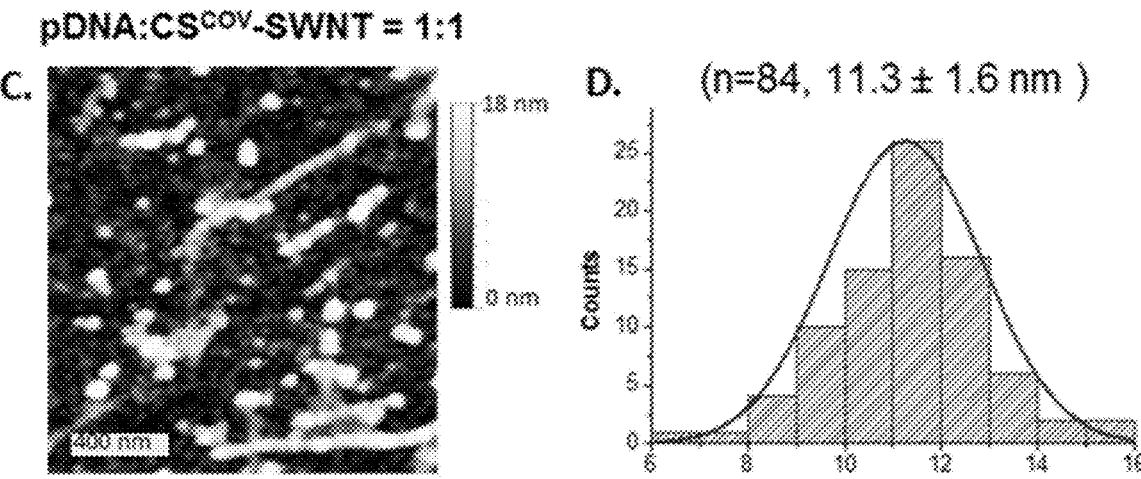
Figure 9C                                    Figure 9D
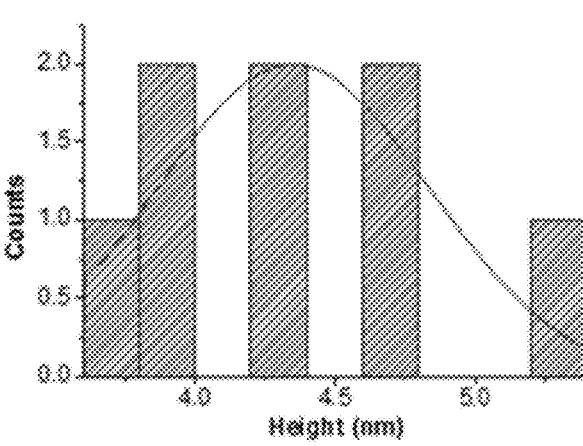
Figure 9E pDNA:CS$^{COV}$-SWNT = 1:6
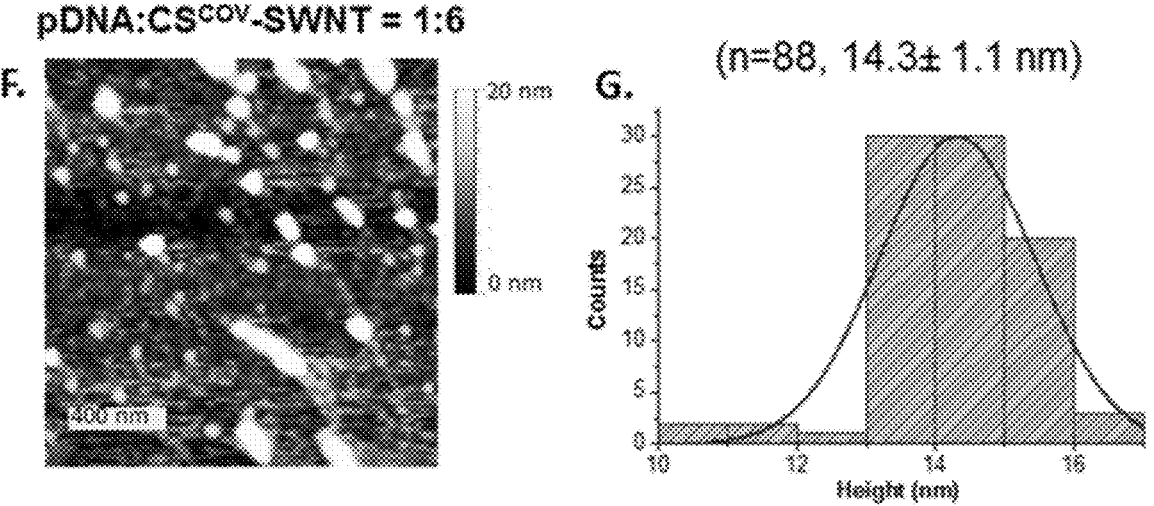
Figure 9F                    Figure 9G
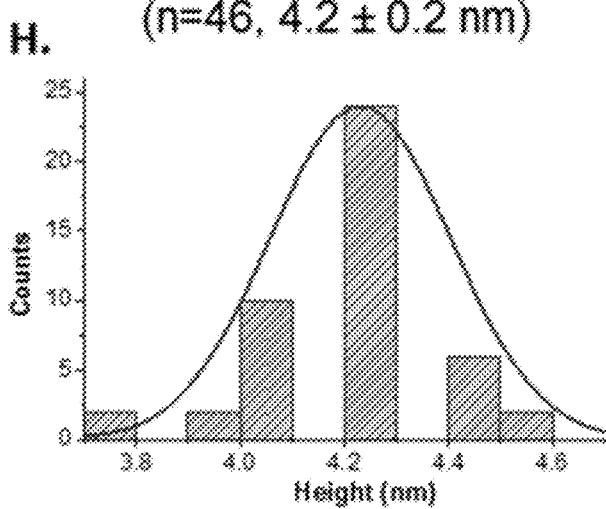
Figure 9H pMBXS1120

8800 bp

Visible                                              nIR

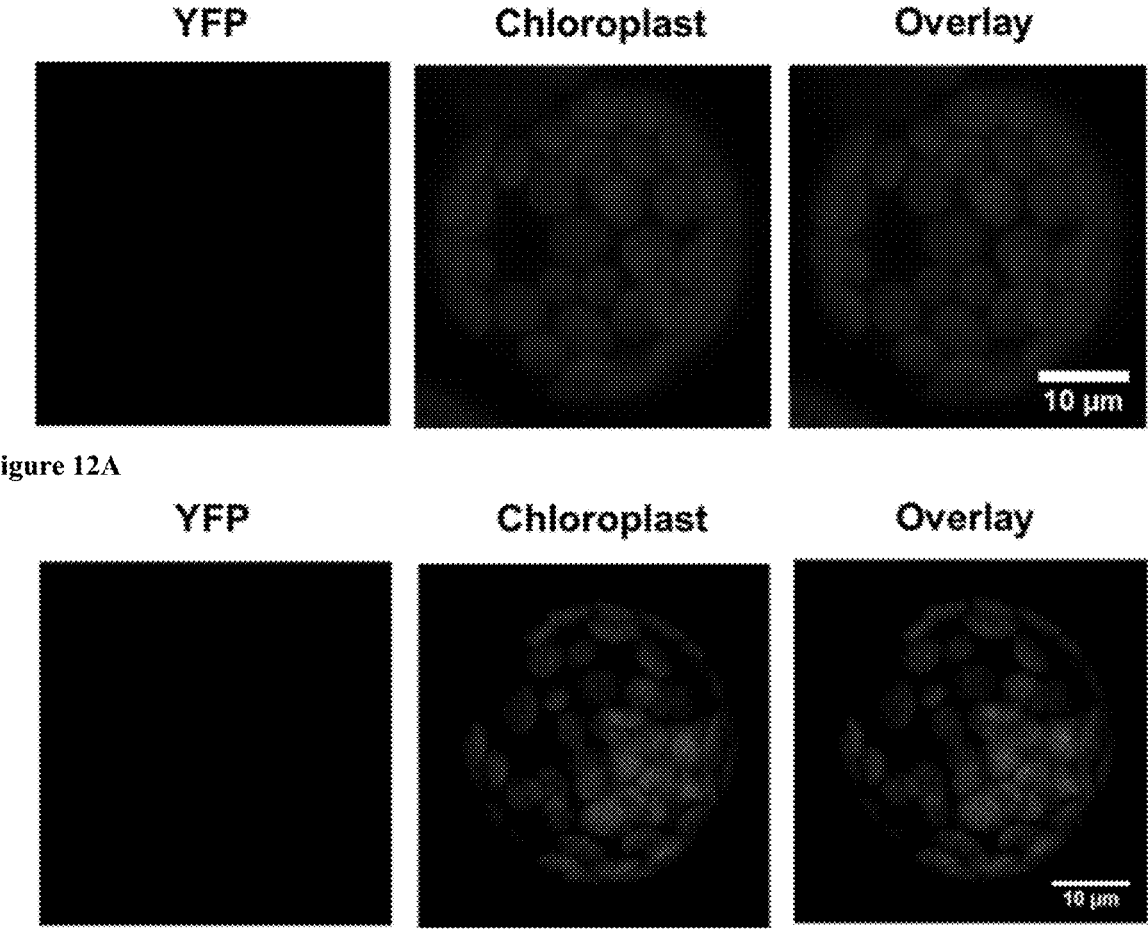
Figure 12A
Figure 12B
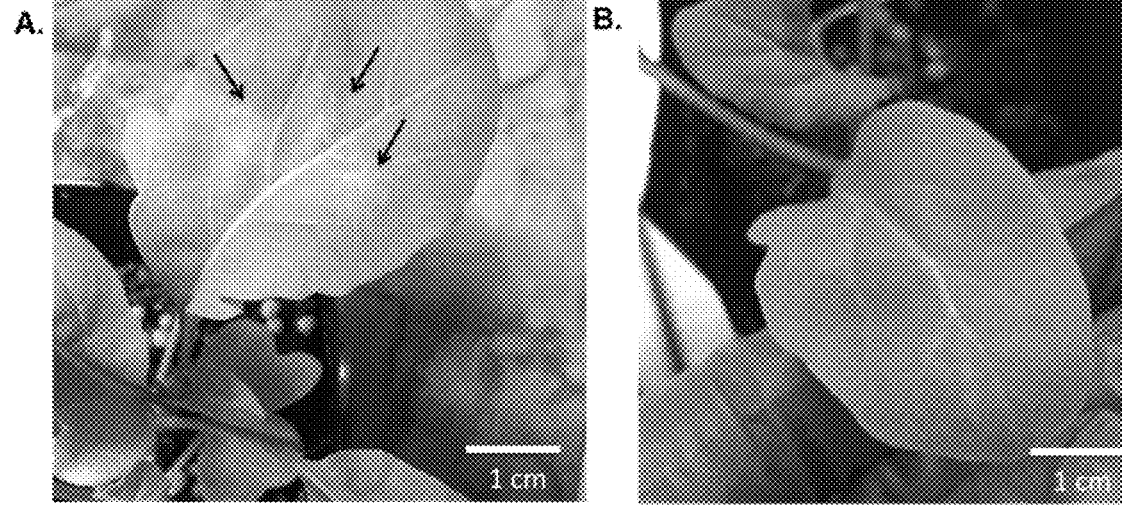
Figure 13A                    Figure 13B

ORGANELLE-SELECTIVE GENE DELIVERY AND EXPRESSION IN THE CHLOROPLAST IN PLANTA USING CHITOSAN-COMPLEXED SINGLE-WALLED CARBON NANOTUBE CARRIERS

CLAIM OF PRIORITY

This application is a National Phase application filed under 35 USC § 371 of International Application No. PCT/US2019/060874, filed on Nov. 12, 2019, which claims the benefit of prior filed U.S. Provisional Patent Application No. 62/758,803, filed Nov. 12, 2018, each of which is incorporated by reference in its entirety.

FIELD OF INVENTION

This invention relates to gene delivery and expression in chloroplasts.

BACKGROUND

Plant genetic engineering is an important tool used in current efforts in crop improvement, pharmaceutical product biosynthesis and sustainable agriculture.

SUMMARY OF THE INVENTION

In one aspect, a composition can include a cationic polymer-complexed nanoparticle complexed with a gene cassette.

In certain circumstances, the gene cassette can include genetic material. The genetic material can be a plasmid DNA.

In certain circumstances, the cationic polymer can include a polysaccharide, a polypeptide, a synthetic polymer, or a natural polymer.

In certain circumstances, the polysaccharide can include dextran, pectin, chitosan, hyaluronic acid, or hydroxyethylcellulose.

In certain circumstances, the polypeptide can include polylysine, polyhistidine, polyarginine, or polyornithine.

In certain circumstances, the synthetic polymer can include polybrene or polyethyleneimine.

In certain circumstances, the natural polymer can include histone or collagen.

In certain circumstances, the polysaccharide can be chitosan. In certain circumstances, the chitosan is deacetylated. The deacetylation can be 10%, 20%, 30%, 40%, 50%, 60%, 70%, 80%, 90% or substantially complete (nearly 100%).

In certain circumstances, the polysaccharide can be pegylated. For example, the polysaccharide can include a polyethyleneglycol polymer having a degree of polymerization of 100 to 10,000, or 1,000 to 8,000, for example, 2,000 or 5,000.

In certain circumstances, the cationic polymer can be covalently bonded to the nanoparticle.

In certain circumstances, the nanoparticle can be a single-walled carbon nanotube.

In certain circumstances, the nanoparticle and the gene cassette can be present in a ratio of 1:1 to 1:10.

In certain circumstances, the gene cassette can include a zinc finger nuclease, a TALEN vector or a CRISPR/Cas9 vector.

In another aspect, a method of delivering genetic material to a plant can include contacting a plant with a composition described herein.

In certain circumstances, the plant can be arugula (*Eruca sativa*), watercress (*Nasturtium officinale*), tobacco (*Nicotiana benthamiana*), spinach (*Spinacia oleracea*) plants or isolated *Arabidopsis thaliana* mesophyll protoplasts.

In certain circumstances, the method can include releasing the genetic material in the interior of a chloroplast.

Other embodiments are described below and are within the claims.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2A shows the relationship between zeta potential of pDNA-SWNT conjugate and the ratio of SWNT:pDNA, FIG. 2B depicts the LEEP model shows that 1:3 and 1:6 pDNA:SWNT ratios (red) have a zeta potential higher than what is required for nanoparticle to enter the chloroplasts, while a 1:1 pDNA:SWNT ratio (black) has lower zeta potential than the threshold. Blue line indicates the threshold zeta potential for nanoparticles to passively traffic into the chloroplasts as predicted by LEEP model. FIG. 2C depicts a representative AFM height image of 1:1 pDNA:$CS^{COV}$-SWNT and its height profile. FIG. 2D depicts a representative AFM height image of 1:6 pDNA:$CS^{COV}$-SWNT and its height profile.

FIG. 3A depicts relative fluorescence intensity of Cy3 dye before and after conjugation with CS-SWNT. When Cy3-ss(GT)$_{15}$ is electrostatically bound to CS-SWNT, the Cy3 fluorescence dye is quenched. $P<0.01$. FIG. 3B depicts percentage of pDNA release from pDNA-SWNT complex in different pH. pDNA is conjugated tightly to chitosan-complexed SWNT at mildly acidic pH (cytosol pH ~5.5) but is slowly released from the pDNA-SWNT conjugates as pH increases (chloroplast stroma pH ~8). The error bars are standard deviations (n=3). FIG. 3C depicts co-localization of CS-SWNT in chloroplast within the isolated protoplasts. Near-infrared fluorescence of SWNTs was observed in chloroplasts under 785-nm laser excitation at 30 mW masked with a 900-nm long-pass filter to remove chloroplast auto-fluorescence. FIG. 3D depicts fluorescence confocal micrographs showing YFP expression from pDNA conjugated to $CS^{COV}$-SWNT (1:6 pDNA:S-WNT w/w ratio) in isolated protoplasts after 24 h.

FIGS. 4A-4H depict chloroplast targeted gene delivery and transient YFP expression in mature arugula plants. Fluorescence confocal micrographs were taken after 2 days of infiltration. FIG. 4A depicts mesophyll cells from leaf infiltrated with 20 mM MES-MgCl$_2$ buffer. FIG. 4B depicts mesophyll cells from leaf infiltrated with pDNA-free chitosan polymer (1:6) without SWNTs. FIG. 4C depicts epidermal cells and FIG. 4D depicts mesophyll cells with pDNA: $CS^{COV}$-SWNT (1:3.4, 1.5 mg L$^{-1}$ of SWNT). FIG. 4E depicts mesophyll cells with pDNA:$CS^{PEG5K}$-SWNT (1:6, 2.5 mg L$^{-1}$ of SWNT). Yellow fluorescent proteins (yellow), chloroplasts (cyan) and cell membrane (red). FIG. 4F depicts mesophyll cells with nuclear targeted pDNA:CS-$^{COV}$-SWNT (1:3, 1.5 mg L$^{-1}$ of SWNT), and FIG. 4G depicts (1:6, 1.5 mg L$^{-1}$ of SWNT). This pDNA is designed for nuclear transformation and contains a GFP marker with a nuclear localization tag. Nucleus stained with DAPI (white), chloroplast autofluorescence (blue), cell membrane stained with FM 4-64 (red). No GFP signal is observed. FIG. 4H depicts viability of arugula plants after infiltration with $CS^{COV}$-SWNTs (2.5 mg L$^{-1}$) and MES buffer (control) as measured by leaf chlorophyll content. There were no significant differences between treatments in the temporal patterns of the normalized chlorophyll index, indicating that $CS^{COV}$-SWNTs do not affect the leaf lifespan. Error bars are standard deviations (n=5).

FIG. 5A depicts mesophyll cells from a watercress leaf infiltrated with pDNA:$CS^{COV}$-SWNT (1:6, 2.5 mg L$^{-1}$ of SWNT). FIG. 5B depicts mesophyll cells from a tobacco leaf infiltrated with pDNA:$CS^{COV}$-SWNT (1:3.4, 1.5 mg L$^{-1}$ of SWNT). FIG. 5C depicts mesophyll cells from a spinach leaf infiltrated with pDNA:$CS^{COV}$-SWNT (1:6, 2.5 mg L$^{-1}$ of SWNT). Yellow fluorescent proteins (yellow), chloroplasts (cyan) and cell membrane (red).

FIG. 6A depicts the peak at 1653.76 cm$^{-1}$, which corresponds to an amide carbonyl carbon (C=O) in chitosan, disappears after deacetylation. FIG. 6B depicts the peak at 3436 cm$^{-1}$ in carboxylated-SWNTs, arising from the O—H stretching of the carboxylic acid group, shifts to a broader peak at 3297 cm$^{-1}$ in $CS^{COV}$-SWNTs due to the N—H bond stretching of chitosan. The peaks at 1654 cm$^{-1}$ and 1570 cm$^{-1}$ in $CS^{COV}$-SWNTs correspond to the C=O bond stretching due to EDC/NHS coupling and N—H deformation in chitosan, further indicating successful conjugation of chitosan through amide coupling reaction. The symmetric stretch of C—O—C group in $CS^{COV}$-SWNTs can also be observed around 1090-1030 cm$^{-1}$.

FIG. 7A-7I depict the mean hydrodynamic radius of chitosan complexed SWNTs and their pDNA conjugates. The aqueous SWNT suspension was kept in room temperature. FIG. 7A depicts CS-SWNTs; as prepared (left) and after 15 days (right), FIG. 7B depicts CS-SWNT after ultracentrifugation at 36,000 rpm for 4 h; as prepared (left) and after 35 days (right), FIG. 7C depicts $CS^{PEG2K}$-SWNTs; as prepared (left) and after 55 days (right), FIG. 7D depicts $CS^{PEG5K}$-SWNTs; as prepared (left) and after 55 days (right), FIG. 7E depicts $CS^{COV}$-SWNTs; as prepared (left) and after 15 days (right), and FIG. 7F depicts pDNA-$CS^{PEG5K}$-SWNT and pDNA-$CS^{COV}$-SWNTs were prepared at pDNA:SWNTs=1:3 in mass ratio. FIG. 7H depicts the mean hydrodynamic radius and FIG. 7I depicts the full-width at half-maximum of chitosan complexed SWNTs and pDNA-SWNT conjugates. Blue bars indicate the properties of as prepared SWNT complexes and red bars indicate those of SWNT complexes after 15-55 days. The aqueous SWNT suspension was kept in room temperature. pDNA-CS$^{PEG5K}$-SWNT and pDNA-CS$^{COV}$-SWNT conjugates were prepared at a 1:3 in mass ratio of pDNA to SWNTs.

FIGS. 8A-8B depict fluorescent confocal micrographs of arugula mesophyll. FIG. 8A depicts control; mesophyll layer with 20 mM MES-MgCl$_2$ buffer. FIG. 8B depicts mesophyll layer with 2 week-old CS-SWNT suspension (3 mg L$^{-1}$) showing significant membrane damage (yellow box). The images were taken after 2 days of infiltration. Chloroplasts (cyan), cell membrane (red).

FIGS. 9A-9H depict AFM images of $CS^{COV}$-SWNTs with and without pDNA. FIG. 9A depicts a representative AFM map of $CS^{COV}$-SWNTs, FIG. 9B depicts histogram of $CS^{COV}$-SWNTs heights extracted from AFM scans, FIG. 9C depicts a representative AFM map of $CS^{COV}$-SWNTs conjugated with pDNA with a 1:1 pDNA:SWNT mass ratio, FIG. 9D depicts histogram of pDNA:$CS^{COV}$-SWNTs 1:1 heights, while a small proportion of bare $CS^{COV}$-SWNTs were also identified and analyzed in FIG. 9E. FIG. 9F depicts a representative AFM map of $CS^{COV}$-SWNTs conjugated with pDNA with a 1:6 pDNA:SWNT mass ratio, FIG. 9G depicts histogram of pDNA:$CS^{COV}$-SWNTs 1:6 heights. FIG. 9H depicts a higher proportion of bare $CS^{COV}$-SWNTs were observed compared to pDNA:$CS^{COV}$-SWNTs 1:1 conjugates and binned separately.

FIGS. 12A-12B depict no YFP expression is detected when *Arabidopsis thaliana* mesophyll protoplasts were incubated with (FIG. 12A) only pDNA, or (FIG. 12B) pDNA:$CS^{COV}$-SWNT conjugate with a pDNA:SWNT ratio of 1:1 (w/w). Scale bar=10 μm.

FIGS. 13A-13B depict the arugula leaf infiltrated with (A) CS-SWNT (5 mg L$^{-1}$) (FIG. 13A) and CS-SWNT (2.5 mg L$^{-1}$) in 2 days (FIG. 13B). Black arrows indicate infiltration spots, which turned yellowish, indicating the onset of leaf senescence. Leaf senescence was not observed in the arugula leaf with CS-SWNT 2.5 mg L$^{-1}$.

FIG. 14B depicts fluorescence confocal micrograph of the arugula leaves infiltrated with pDNA: $CS^{COV}$-SWNT conjugates (1.5 mg L$^{-1}$, pDNA:SWNT=1:6) after 2 days. The cell membrane is stained with FM 4-64 (red).

FIG. 15A depicts fluorescent confocal microscope image of Alexa Fluor 488-conjugated $CS^{COV}$-SWNT at a 3:1=SWNT:dye (w/w) ratio (zeta potential 29.2 mV) within the chloroplasts. FIG. 15B depicts fluorescent confocal microscope image of Alexa Fluor 488-conjugated $CS^{COV}$-SWNT at a 0.75:1=SWNT:dye (w/w) ratio (zeta potential 19.7 mV) within the cytosol not the chloroplasts. Yellow (Alexa Fluor 488), blue (chloroplasts), red (cell membrane), FIG. 15C depicts the estimated co-localization efficiency of dye-labeled SWNTs within the chloroplasts. Fluorescent confocal microscope images were obtained after 2 h infiltration of dye-labeled SWNT (2.5 mg L⁻¹) into 3.5 week-old watercress plants.

DETAILED DESCRIPTION

Figure 1A:
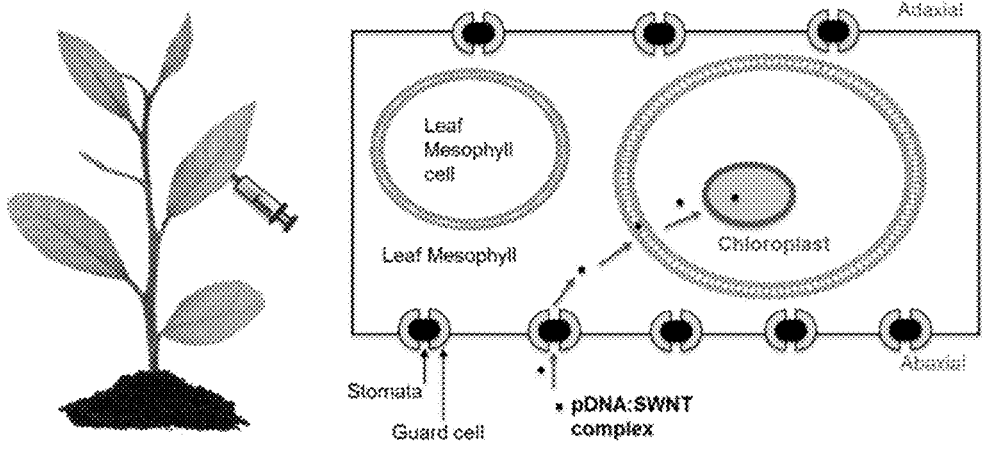
FIG. 1A is a schematic illustration of chloroplasts-targeted delivery of plasmid DNA (pDNA) by using SWNTs in a plant leaf. pDNA:SWNT complexes enter the leaf mesophyll through stomata pores, traverse plant cell walls, plasma membranes, and eventually chloroplast bilayers. Negatively charged pDNA is condensed to the positively charged surface of chitosan-complexed SWNTs via electrostatic interaction.

Conventional genetic engineering techniques target the nuclear genome, prompting concerns about the proliferation of foreign genes to weedy relatives. Chloroplast transformation does not have this limitation, since the plastid genome is maternally inherited in most plants, motivating the need for organelle-specific and selective nanocarriers. Herein, chitosan-complexed single-walled carbon nanotubes (SWNTs) are designed, utilizing the Lipid Exchange Envelope Penetration (LEEP) mechanism. The SWNTs function as nanocarriers to selectively deliver plasmid DNA (pDNA) to chloroplasts of different plant species without external biolistic or chemical aid. In addition, the pDNA unloading mechanism is validated within the chloroplast stroma. Chloroplast-targeted transgene delivery and transient expression in living mature arugula (*Eruca sativa*), watercress (*Nasturtium officinale*), tobacco (*Nicotiana benthamiana*) and spinach (*Spinacia oleracea*) plants in planta and in isolated *Arabidopsis thaliana* mesophyll protoplasts is demonstrated. This nanoparticle-mediated chloroplast transgene delivery tool provides practical advantages over current delivery techniques as a potential transformation method for mature plants to benefit plant bioengineering and biological studies.

Recent developments in the genetic engineering of plants during the last decade have enabled advances in agriculture, pharmaceutical biosynthesis, and fundamental plant biology. See, references 1-8. Transgenic plants have been used extensively in commercial agriculture to provide herbicide tolerance and pest resistance for major food and feed crops. See, reference 9. They also represent an attractive, cost-efficient vehicle for the production of antibodies and pharmaceuticals due to the ability to scale up plant biomass with low cost and maintenance requirements. See, reference 10. Expensive fermentation and complex purification processes associated with mammalian and bacterial-based systems could be eliminated if the plant tissues expressing recombinant antigens are used as edible vaccines. See, reference 11. However, there are commercial and environmental issues with conventional technologies of plant genetic engineering, in which transgenic plants are generated by transformation of the nuclear genome. The random location of nuclear chromosomal insertions from conventional transformation techniques leads to time-consuming screening of large numbers of transgenic plants to find suitable lines. See, reference 12. Commercialization of transgenic lines is time consuming and costly due to the lengthy regulatory process for bringing transgenic lines to market. See, reference 13. The environmental concerns include the undesirable spread of foreign genes from transgenic crops to their weedy relatives. See, reference 14.

Chloroplast transformation offers advantages over conventional nuclear transformation technologies and thus represents a viable alternative approach for plant genetic engineering. See, references 15-17. Due to maternal inheritance of plastid genomes in most higher plants, chloroplast transformation provides a level of containment that rarely leads to genetic outcrossing of transgenes. See, references 18 and 19. Since the plastid genome is highly polyploid, transformation of chloroplasts can lead to extraordinarily high levels of foreign protein production by introducing thousands of copies of foreign genes per plant cell. See, reference 20. In addition, the reduced risk of mammalian viral contaminants and the ability of chloroplasts to fold human proteins has enabled high-yield production of human therapeutics. See, references 21 and 22. Chloroplasts can withstand stressful conditions such as high salt or drought, thereby the integrity of the products derived from chloroplast transformation can be better preserved. See, reference 18. Chloroplast transformation is typically achieved by bombardment of plant tissue using a biolistic device or by polyethylene glycol (PEG)-mediated transformation. See, references 23 and 24. However, PEG-mediated transformation requires time-consuming isolation and regeneration of protoplasts, the efficiency of which is highly species- and tissue-dependent, while particle bombardment requires expensive, specialized devices and often leads to significant damage to the plant tissue. See, references 25 and 26. In addition, routine plastid transformation is difficult, if not impossible, to achieve in many plant species using these techniques. See, references 27 and 28. Hence, an alternative approach to deliver plasmid DNA (pDNA) for chloroplast transformation is necessary to address these shortcomings.

Nanoparticle-mediated transformation represents a promising approach for plant genetic engineering. Although nanoparticles have been widely studied to deliver biomolecules to animal cells and tissues in recent years, their use in plants is limited due to their potential toxicity and limited knowledge of how they interact with plant biological membranes and the multilayered cell wall. See, references 25 and 29-32. The biolistic approach has previously been employed to deliver mesoporous silica nanoparticles containing genetic materials and chemicals past the rigid cell wall into the cytosol of plant protoplasts and seedlings. See, reference 33. However, nanoparticle-mediated gene delivery into a specific organelle of mature plants without external mechanical aid has not been demonstrated. Specifically designed nanoparticles, including single-walled carbon nanotubes (SWNTs), can traverse the rigid plant cell walls, membranes and even the double lipid bilayers of chloroplasts before they become kinetically trapped within the chloroplasts. See, reference 34. This passive nanoparticle uptake mechanism was described using a mathematical model called Lipid Envelope Exchange Penetration (LEEP), whereby the ability of nanoparticles to penetrate the cell membrane and the double lipid bilayer of chloroplasts is governed primarily by nanoparticle size and surface charge. See, references 35 and 36. Based on this mechanism, the tunable physical and optical properties of nanomaterials can be leveraged to optimize the passive delivery of biological cargoes across many plant barriers that have hitherto been difficult to access. The study is theoretically not limited to SWNTs. SWNTs were selected out of various nanomaterials because SWNTs have attracted considerable interest as nanocarriers for drug and gene delivery due to their high aspect ratio and large surface area for chemical modification. See, references 37 and 38. However, existing applications of SWNTs in plants were primarily limited to studies of SWNTs transport in plant tissues or cells, and none of the work explored the possibility of utilizing SWNTs as nanocarriers for gene delivery into specific plant organelles. See, reference 39. Chitosan-wrapped single-walled carbon nanotubes (CS-SWNTs) possess sufficiently high surface charge to allow them to passively penetrate the plant membrane and double lipid bilayers of chloroplasts. See, reference 34. For successful gene delivery, the pDNA has to be condensed by chitosan-functionalized SWNTs, safely transported to the chloroplasts after crossing various plant membranes, intracellularly detached and transiently expressed within the chloroplast stroma. The potential use of chitosan as a polycationic gene carrier for plant transformation is implied by its capability to form a complex with negatively charged pDNA via electrostatic interactions, protecting pDNA from nuclease degradation. In addition, chitosan is a biodegradable polysaccharide, abundant in nature and non-toxic to plant systems. See, references 40-43.

Figure 1B:
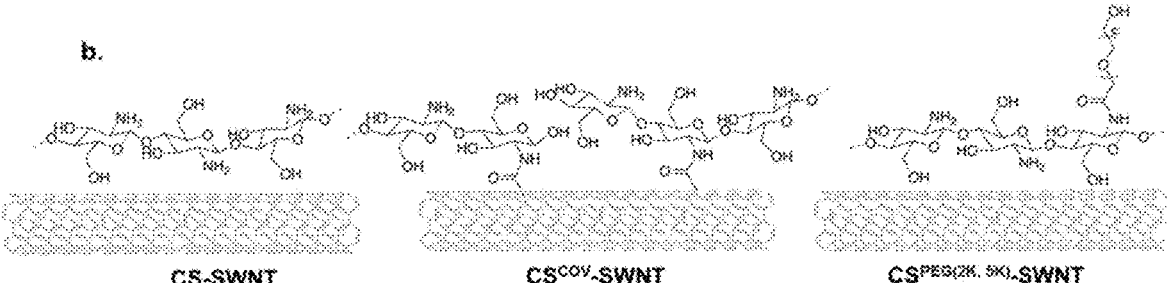
FIG. 1B is a depiction of the chemical structure of chitosan-complexed SWNTs and their denotations; chitosan-SWNTs (CS-SWNTs), PEGylated chitosan-SWNTs ($CS^{PEG}$-SWNT with PEG5K and PEG2K), and covalently bonded chitosan to the carboxylated SWNTs ($CS^{COV}$-SWNTs).

As described herein a gene delivery carrier, based on SWNTs, can leverage the LEEP mechanism to selectively carry a gene cassette to the plant chloroplasts. Gene delivery in planta is shown by visualization of transient expression of a marker gene after infusion of the nanoparticle carriers to the leaf lamina (FIG. 1A). Four kinds of chitosan-complexed SWNTs were designed by non-covalent wrapping and covalent modification of the nanotube sidewall to improve pDNA loading and delivery efficiency to the chloroplasts (FIG. 1B). This strategy is vastly different from fabricating single-stranded DNA (ssDNA)-wrapped SWNTs, where ssDNA is strongly adsorbed to the nanotube surface and its detachment is only possible in harsh conditions. See, reference 44. This study is the first demonstration of a nanoparticle-mediated approach capable of enabling chloroplast-selective gene delivery for transgene expression in mature non-model plants, without the aid of external chemical or mechanical force.

Figure 6A:
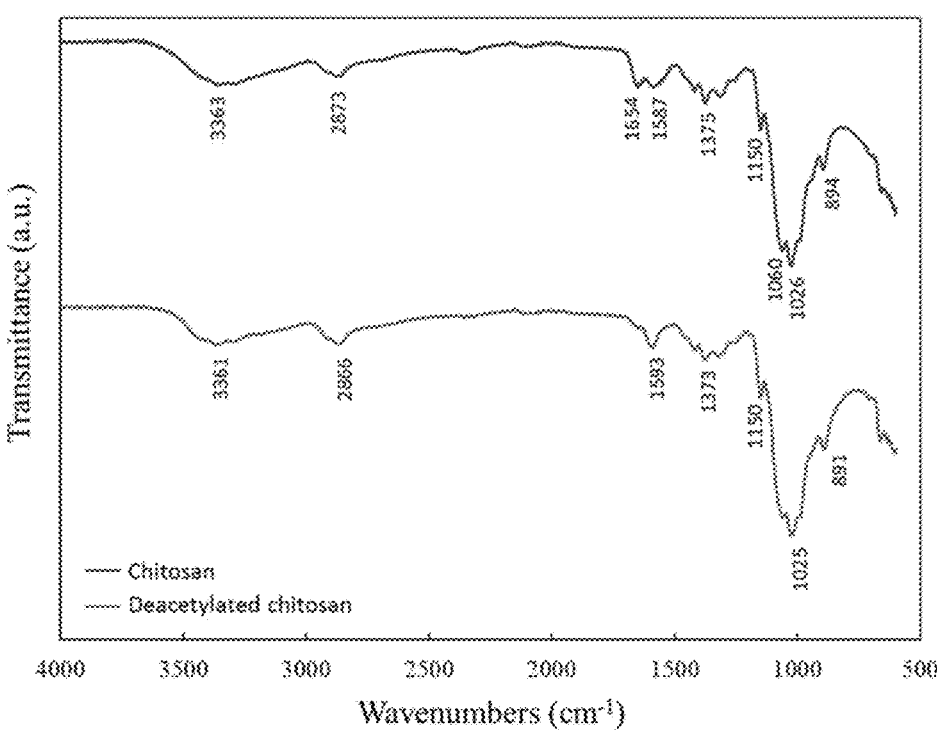
FIGS. 6A-6B depict FT-IR spectra of chitosan and deacetylated chitosan.
Figure 6B:
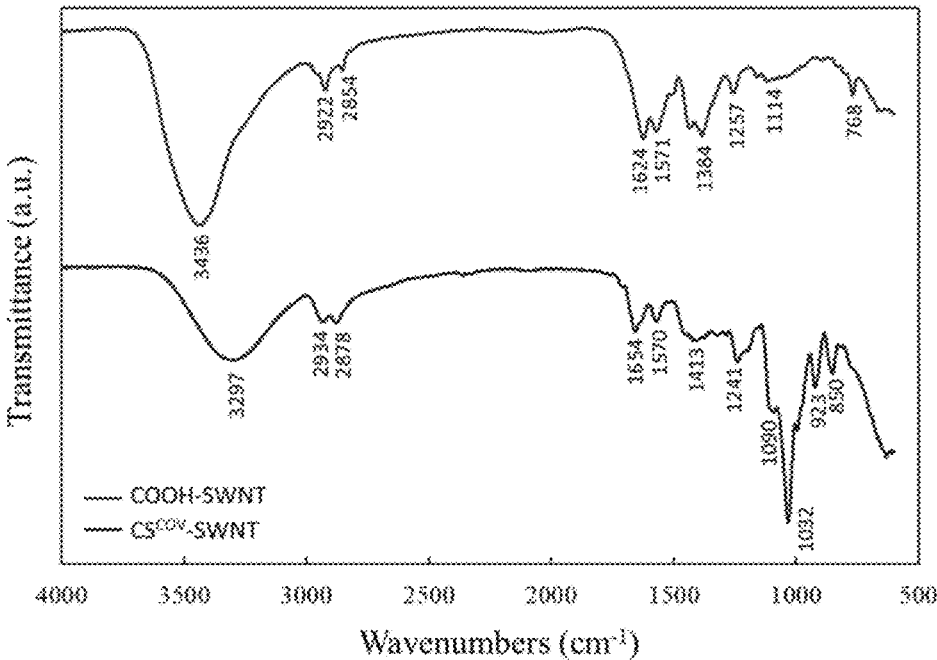
Figure 7A:
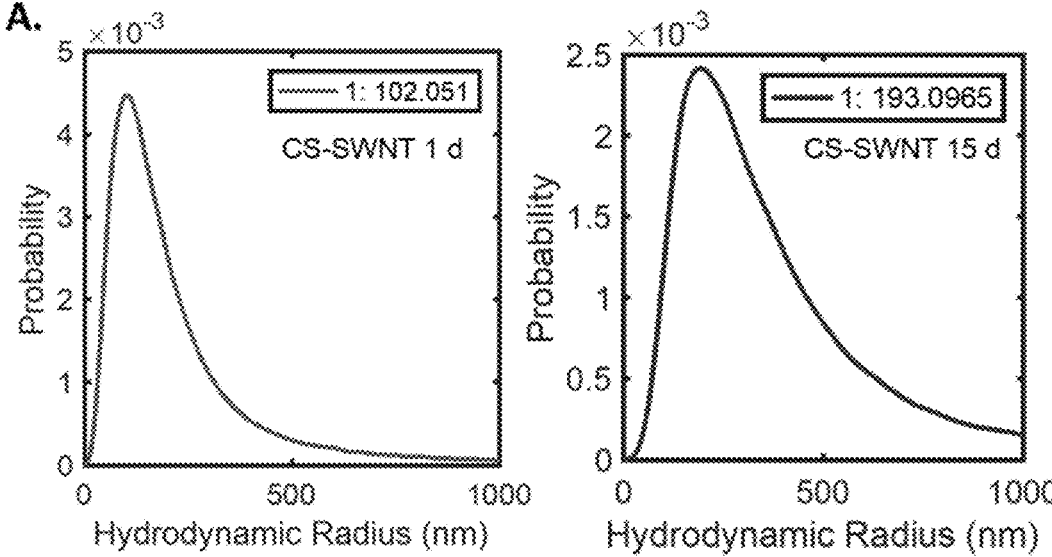
Figure 7B:
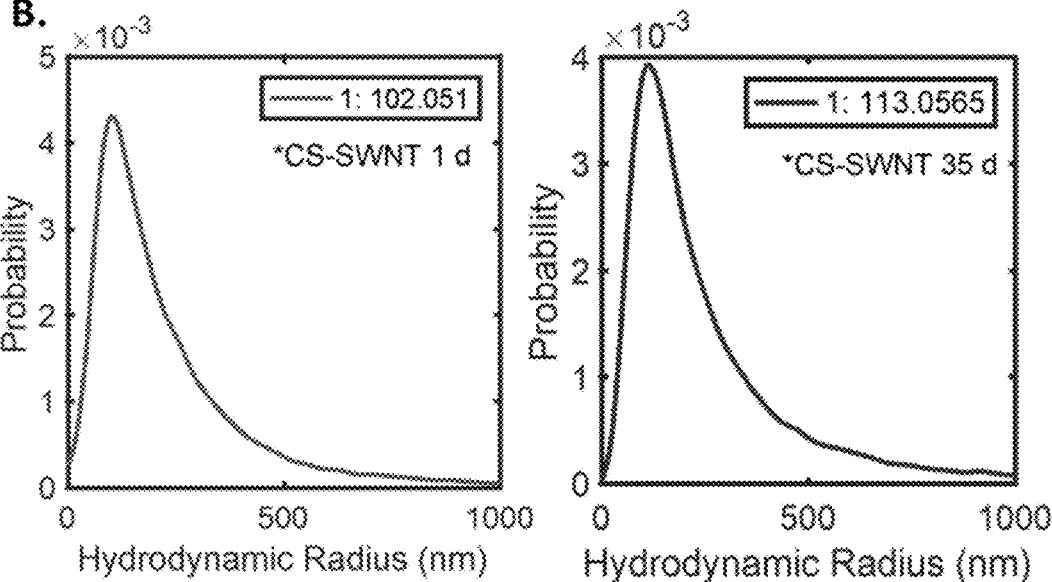
Figure 7C:
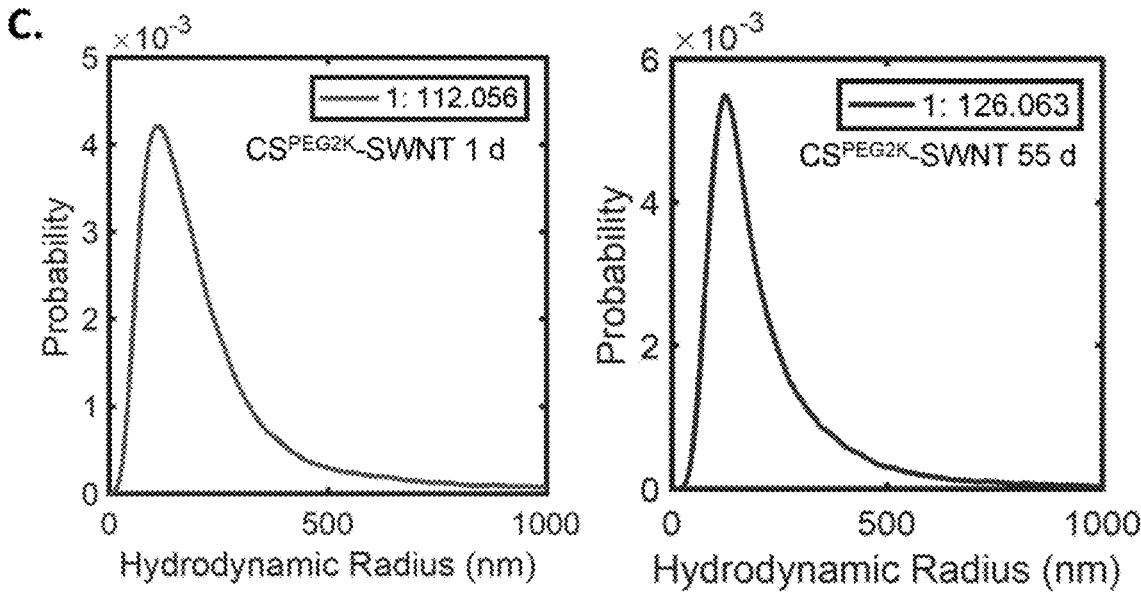
Figure 7D:
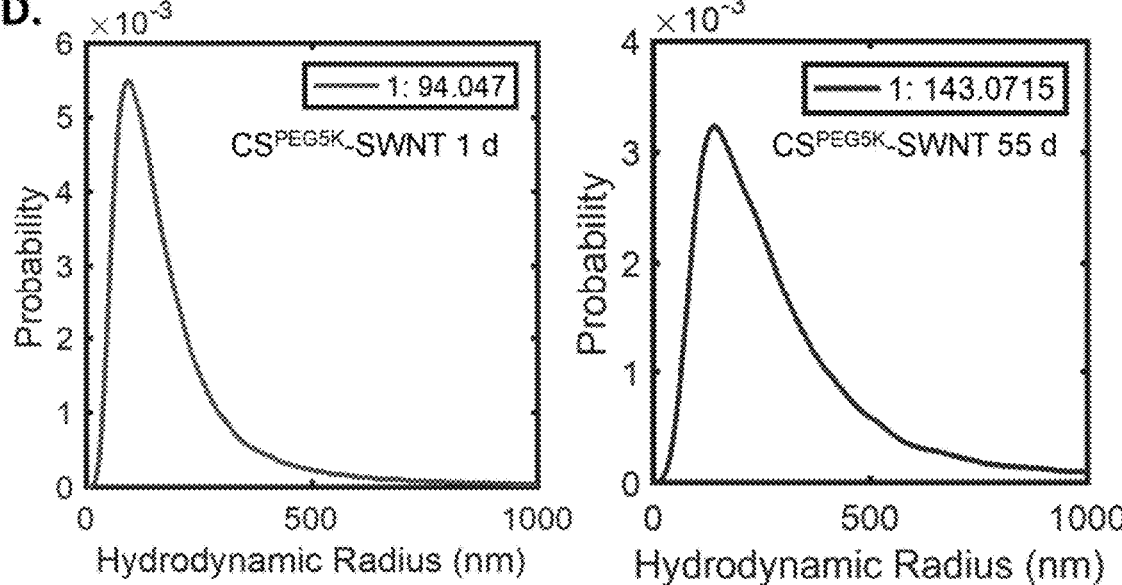
Figure 7H:
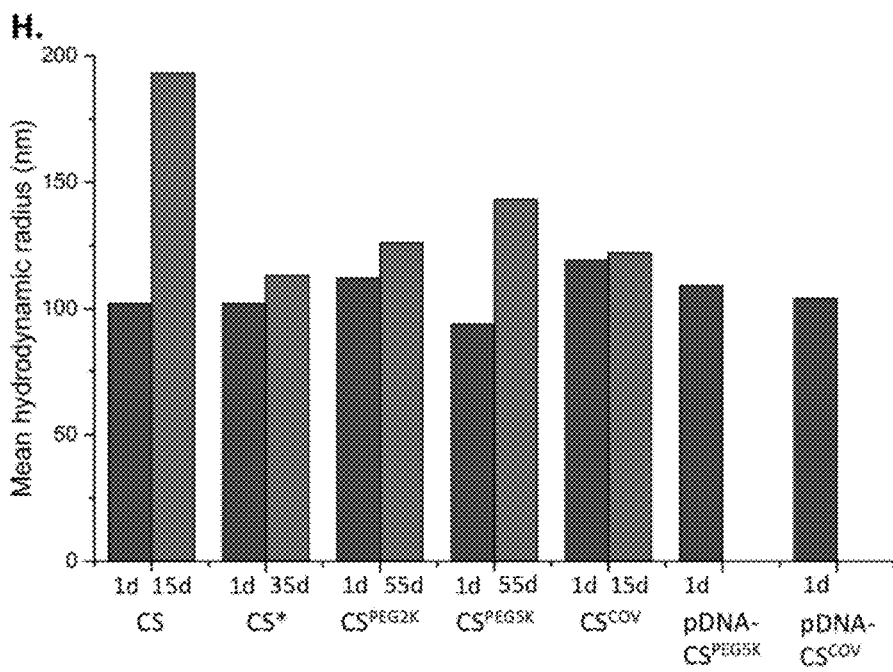
Figure 7I:
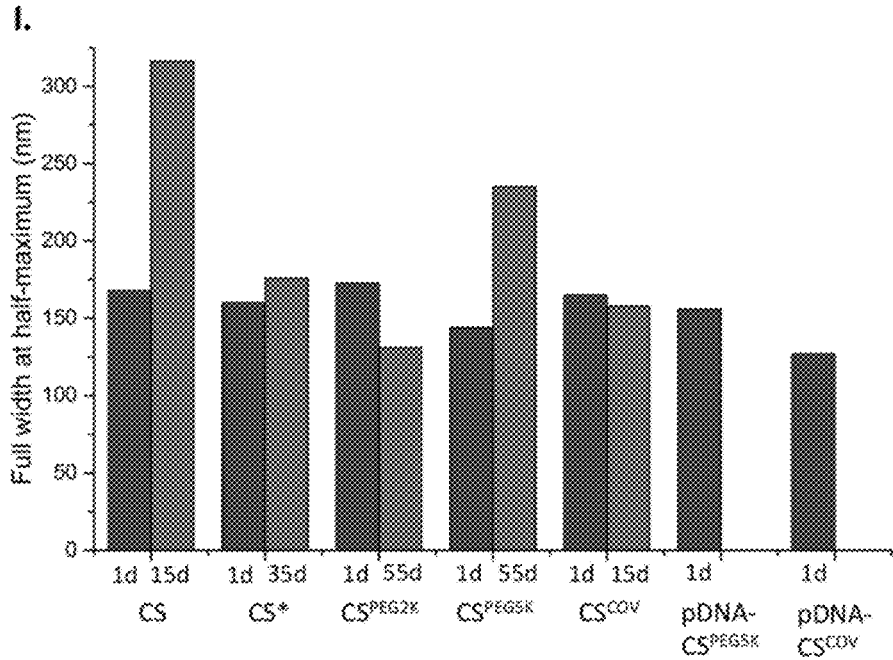

Four different chitosan-complexed SWNTs were prepared, which were rationally designed as a cationic nanocarrier capable of loading the pDNA vector and releasing the pDNA selectively in the chloroplasts. As the deacetylation degree of chitosan has a significant effect on DNA loading capacity, deacetylated chitosan was used to prepare CS-SWNTs to increase pDNA loading efficiency. See, reference 45. The deacetylation of chitosan was confirmed by the disappearance of C=O peak at 1654 cm$^{-1}$ through Fourier transform infrared (FT-IR) spectroscopy (FIG. 6A). Polyethylene glycol (PEG, Mw. 2000 and Mw. 5000) modified chitosan-wrapped SWNT (CS$^{PEG2K}$-SWNTs and CS$^{PEG5K}$-SWNTs) was synthesized to enhance the nanocarriers' colloidal stability as the PEG chain has been demonstrated to increase nanoparticle repulsion in various salt concentrations and assist the delivery of biomolecular cargo past lipid bilayers. See, references 46 and 47. 0.1 equiv. of PEG chain was coupled to CS-SWNTs to retain a net positive charge of nanocarriers for pDNA condensation. Besides non-covalent functionalization of SWNTs, the effect of covalently functionalized SWNTs was also investigated, in which deacetylated chitosan molecules are covalently bonded to carboxylated-SWNTs (CS$^{COV}$-SWNTs) through EDC/NHS coupling to obtain more stable chitosan functionalization across various biological barriers in the plant, as well as within plant subcellular compartments. The covalent attachment of chitosan onto the sidewall of carboxylated-SWNTs was confirmed by FT-IR spectroscopy (FIG. 6B). The peaks at 1654 cm$^{-1}$ and 1570 cm$^{-1}$ in CS$^{COV}$-SWNTs correspond to the C=O bond stretching due to the amide bond, indicating successful conjugation of chitosan.

To monitor the colloidal stability of chitosan-complexed SWNTs, the particle size distribution of chitosan-complexed SWNTs was analyzed by nanoparticle tracking analysis (NTA), which captures the Brownian trajectories of individual nanoparticles in solution. The mean equivalent hydrodynamic radius of as-prepared CS-SWNTs is 102 nm after ultracentrifugation at 36,500 rpm at 15° C. for 4 h to remove SWNT bundles (FIG. 7A-7I). The nanoparticle suspension did not show any significant increase in size for more than a month when stored in ambient conditions. On the other hand, without extensive purification, CS-SWNTs easily aggregated as shown by the doubling in mean size (193 nm) after 2 weeks (FIG. 7A-7I). Chemically modified chitosan-complexed SWNTs such as CS$^{PEG2K}$-SWNTs, CS$^{PEG5K}$-SWNTs, and CS$^{COV}$-SWNTs exhibited a mean equivalent hydrodynamic radius of 94-119 nm and maintained excellent colloidal stability for several weeks in water at room temperature. As aggregated SWNT bundles induce significant damage to the plant cell membrane (FIG. 8A-8B), only chitosan-complexed SWNTs with a mean equivalent hydrodynamic radius less than 120 nm were used for pDNA delivery into living plants.

Figure 2A:
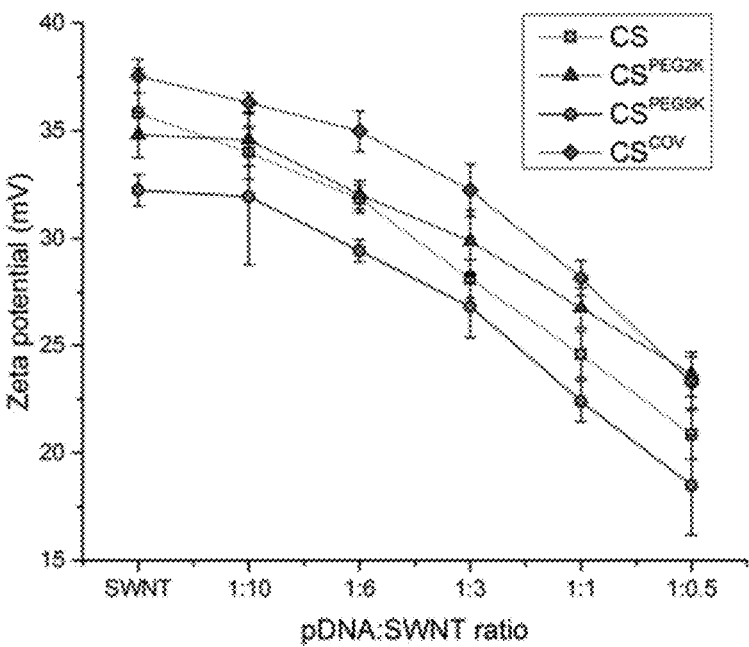
FIGS. 2A-2D depict the optimal pDNA loading on SWNTs for high efficiency trafficking of the nanocarriers into the chloroplast.
Figure 2B:
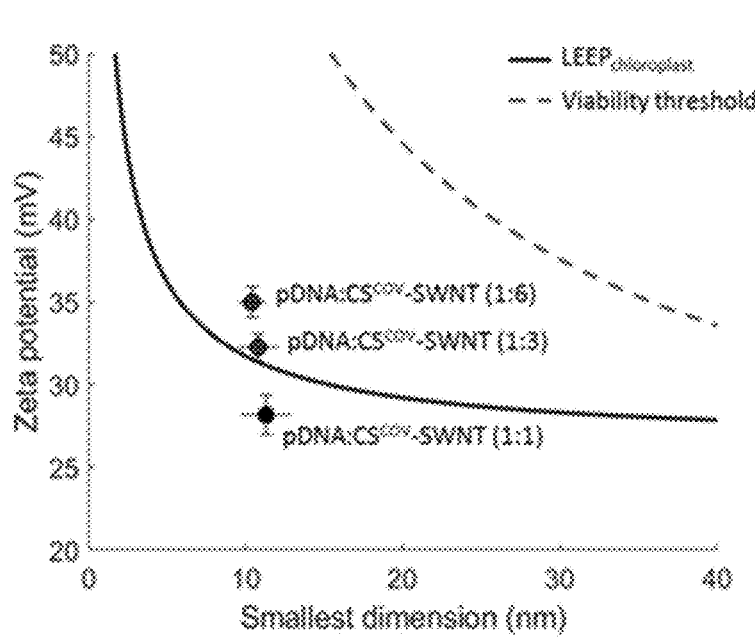

The negatively charged pDNA was complexed with polycationic chitosan-complexed SWNTs through electrostatic interaction by incubation in 20 mM MES buffer (pH 5.7). Previously proposed an experimentally-validated LEEP model was proposed, which asserts that the ability of a nanoparticle to passively traffic through the plasma membrane and chloroplast double lipid bilayers is primarily governed by the size and surface charge of the nanoparticle (Equation 1):

$$\xi^* = \pm\left(\frac{\varepsilon_M + \varepsilon_W}{\varepsilon_W}\right)\left(\frac{d}{a}\right)e^{\kappa(d-a)}\sqrt{\frac{(\Gamma - a\gamma_0 + 4a\Delta\Delta H\rho_n)L}{2a\varepsilon_0\varepsilon_M\left(1 - \frac{\varepsilon_M}{\varepsilon_W}\right)}} \quad \text{(Equation 1)}$$

where $\xi^*$ is the threshold zeta potential for nanoparticle entry into the chloroplast, $\varepsilon_M$ and $\varepsilon_W$ are relative permittivity of the chloroplast double lipid bilayers (2.2) and the medium (80) respectively, d is the effective charge radius, $\alpha$ is the nanoparticle radius, $\kappa^{-1}$ the Debye-Huckel screening length, $\Gamma$ is the pore line tension (10$^{-12}$ N), $\gamma_0$ is the resting membrane tension (0.6 mN/m), $\Delta\Delta H$ is the change in free energy due to lipid binding on the nanoparticle (0.05 k$_b$T), $\rho_n$ is the lipid density on the nanoparticle (10$^{18}$), and L is the approximate thickness of the membrane dielectric (1.1× 10$^{-10}$ m). See, references 35 and 48-52. The surface charge of pDNA-SWNT conjugates at various pDNA:SWNT ratios were also investigated to determine the optimal pDNA loading on SWNTs for high nanocarriers' efficiency to passively traffic into the chloroplasts according to the LEEP model (FIG. 2A). It was found that at a pDNA:SWNT ratio lower than 1:1 (w/w), the pDNA-SWNT conjugates have an overall zeta potential higher than the threshold predicted by our LEEP model to be kinetically trapped inside the chloroplasts, and lower than the predicted maximum value that allows them to traverse past the plant cell membrane without causing cell damage (FIG. 2B). See, reference 36. When the pDNA:SWNT ratio exceeds 1:1, physical aggregation of SWNTs could be seen with the naked eyes. This may be due to weaker electrostatic repulsion between nanoparticles with lower surface charge, resulting in decreased colloidal stability. However, the increase in size distribution could not be detected by the NTA method as it can only capture the trajectories of particles with equivalent hydrodynamic radius between 10 and 1000 nm. The zeta potential and hydrodynamic radius of the four chitosan-complexed SWNTs and the pDNA:SWNT 1:3 conjugates are summarized in Table 1.

TABLE 1

Summary of surface zeta potential and hydrodynamic
radius of different SWNTs and pDNA-SWNT conjugates.

| | SWNTs | | | pDNA:SWNTs (w/w) 1:3 | | |
|---|---|---|---|---|---|---|
| | Zeta potential (mV) | Mean hydrodynamic radius (nm) | FWHM of hydrodynamic radius distribution (nm) | Zeta potential (mV) | Mean hydrodynamic radius (nm) | FWHM of hydrodynamic radius distribution (nm) |
| CS-SWNT | 35.8 | 102 | 160 | 28.1 | 190 | 275 |
| $CS^{PEG2K}$-SWNT | 34.8 | 112 | 173 | 29.9 | 107 | 148 |
| $CS^{PEG5K}$-SWNT | 32.2 | 94 | 144 | 26.8 | 109 | 156 |
| $CS^{COV}$-SWNT | 37.6 | 119 | 165 | 32.3 | 104 | 127 |

Figure 2C:
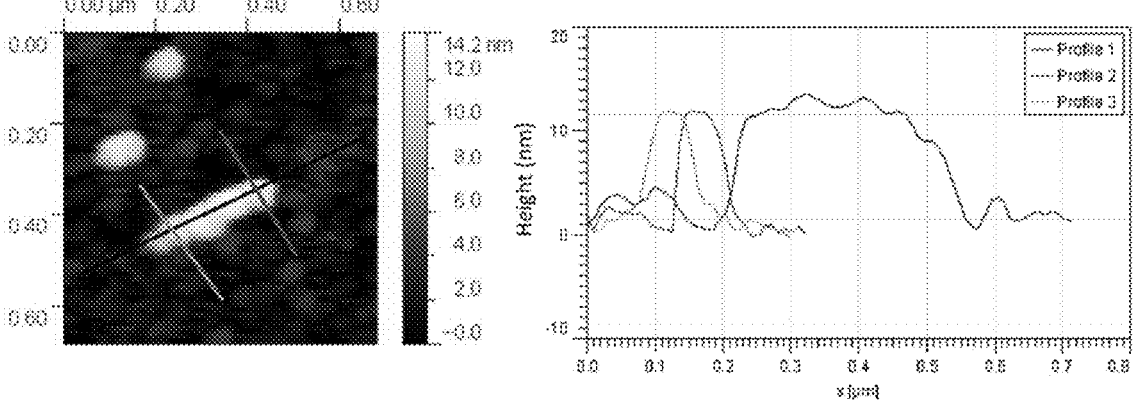
Figure 2D:
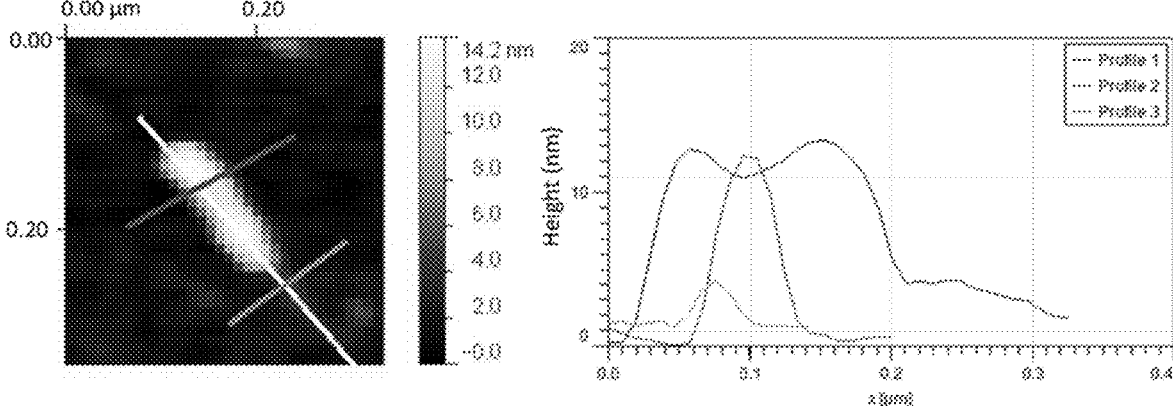

The effect of pDNA binding on the nanocomplexes' height was analyzed by atomic force microscopy (AFM) measurement. The height of $CS^{COV}$-SWNTs without pDNA binding was found to be 3.9±0.9 nm (n=50) (FIG. 9A-9H). The height of the pDNA-$CS^{COV}$-SWNT conjugates was 11.3±1.6 nm. Interestingly, the surface coverage of pDNA on the nanotube surface in pDNA:$CS^{COV}$-SWNT 1:1 conjugate is more than 91% (n=91), whereas 1:6 conjugates displayed a lower surface coverage of 66% (n=134) (FIG. 9A-9H). The height profile of the pDNA:$CS^{COV}$-SWNT 1:1 conjugate was uniform at 12 nm along the nanotube length (FIG. 2C), demonstrating almost complete coverage of nanotubes by pDNA. In the pDNA:$CS^{COV}$-SWNT 1:6 conjugate, two distinct height distributions of 12 nm and 4 nm along the same nanotube length (FIG. 2D) were found, demonstrating partial coverage of pDNA on an individual nanotube surface.

Figure 3A:
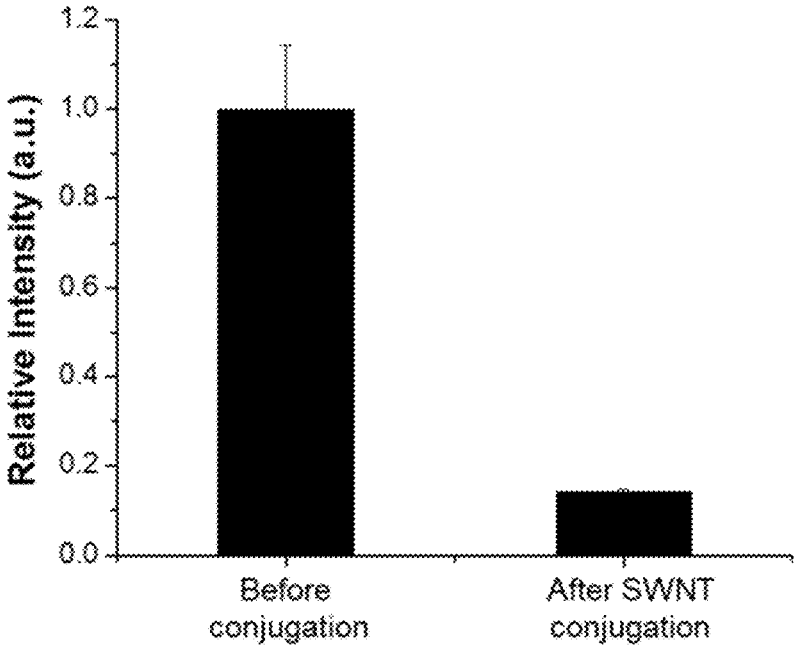
FIGS. 3A-3D depict release of DNA from DNA-chitosan complexed SWNT conjugates in vitro and transgene expression in isolated protoplasts.
Figure 3B:
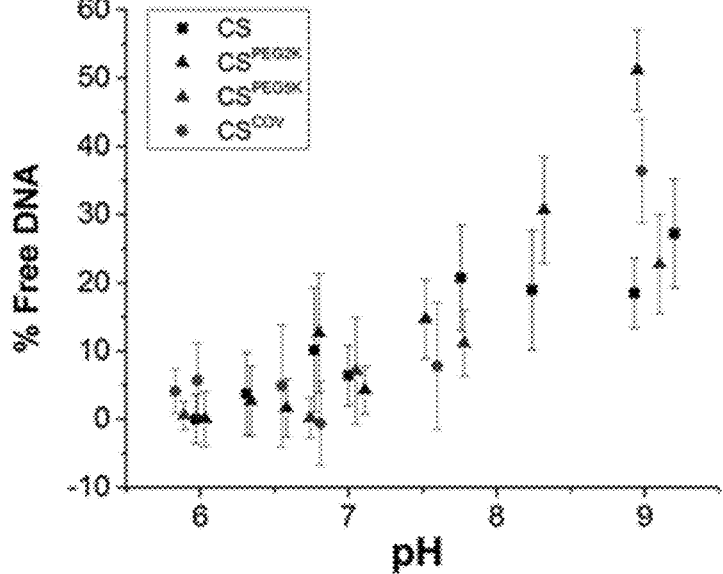

It is known that the pH of the biological environments strongly influences the electrostatic interaction between cationic polymer and anionic DNA molecules. See, reference 53. The question of how the pH of different compartments within plant cells could affect the conjugation efficiency of pDNA to our polycationic nanocarriers was investigated. The pH of the plant cell cytosol is reported to be around 5.5, while the pH of the chloroplast stroma is found to be higher at around 8. See, reference 54. Chitosan was chosen as a cationic polymer wrapping in this study as its primary amines have a pKa of 6.5, below which the amine groups are protonated and can bind strongly to pDNA. See, reference 55. In the weakly basic environment within the chloroplast stroma, it was predicted that pDNA can be released efficiently from pDNA-SWNT conjugates due to weaker electrostatic attraction between pDNA and the primary amine groups of chitosan. Hence, our chitosan-complexed SWNT carriers are designed to bind tightly onto pDNA in the extracellular environment and within the cytosol, before the carriers unload the pDNA inside the chloroplasts to accomplish selective chloroplast-targeted gene delivery. To demonstrate the release of pDNA from chitosan-complexed SWNTs in a basic pH environment, a fluorescent dye-labeled single-stranded DNA (Cy3-ss(GT)$_{15}$)-chitosan SWNT assembly as a pDNA-SWNT mimetic was prepared. The quenching and de-quenching of fluorophore in the proximity of SWNT surface due to energy and electron transfer processes can be used as a marker to quantify the degree of detachment of fluorescently-labeled DNA. See, references 56 and 57. When Cy3-ss(GT)$_{15}$ is electrostatically bound to the cationic chitosan surface of the SWNT, the Cy3 fluorescence dye is quenched by nearly 85% (FIG. 3A). A restoration of the Cy3 fluorescence indicates that Cy3-labeled DNA strands are desorbed from the chitosan-functionalized SWNT surface and exist in free form. See, reference 56. All of the chitosan-complexed SWNTs are found to release DNA strands above pH 7.5 (FIG. 3B).

Figure 3C:
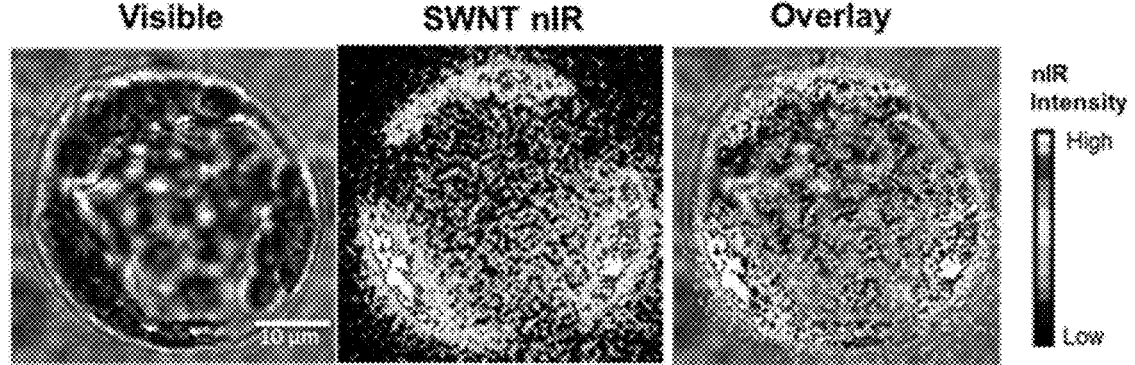
Figure 3D:
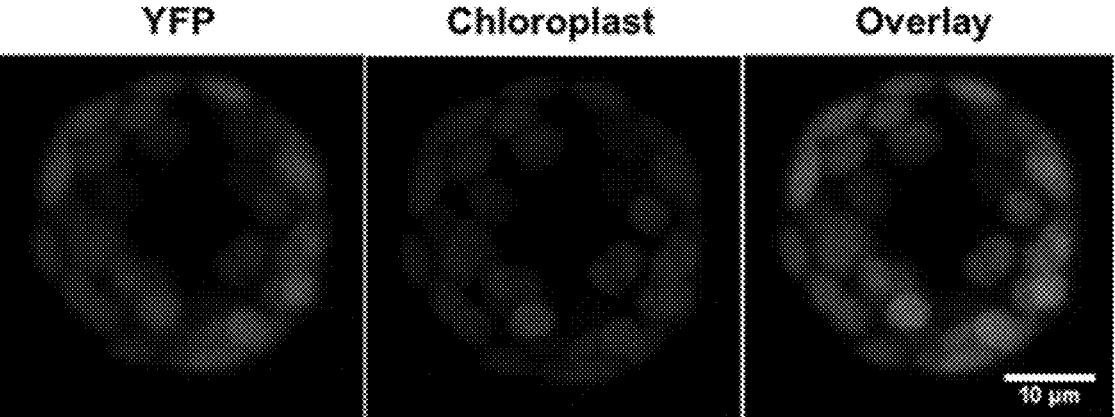
Figure 10:
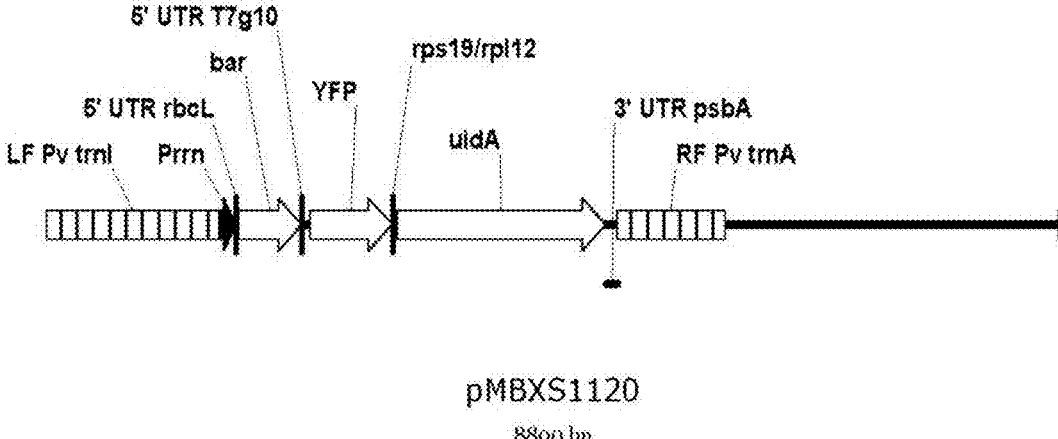
FIG. 10 depicts a plasmid map of pMBXS1120.
Figure 11:
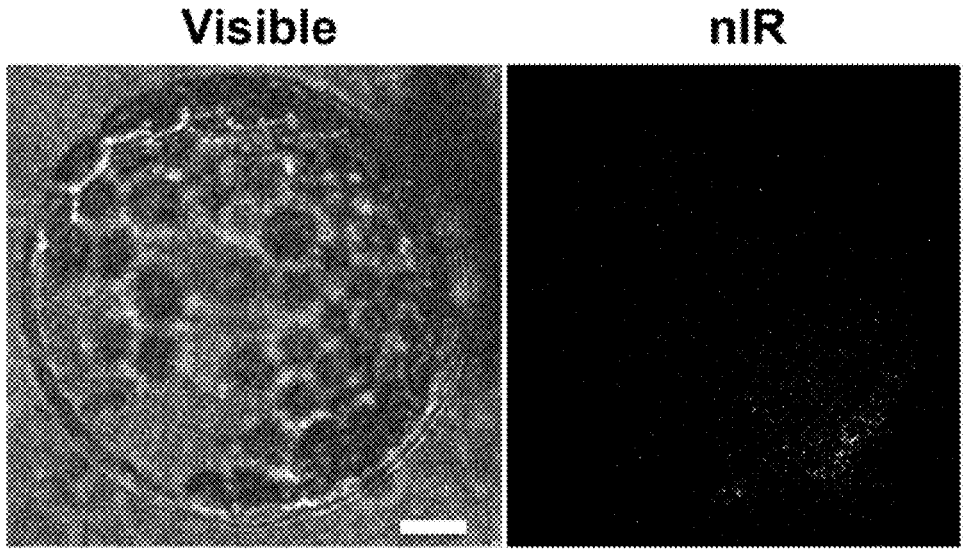
FIG. 11 depicts autofluorescence of chloroplasts under 785 nm laser at 30 mW, which is masked with a 900 nm-long pass filter. The scale bar is 10 μm.

To demonstrate in vitro DNA delivery and transient expression in the chloroplast using our chitosan-complexed SWNT carriers, Arabidopsis thaliana mesophyll protoplasts and incubated them with pDNA-SWNT conjugates was isolated. As a model system, pDNA (pMBXS1120, FIG. 10) encoding yellow fluorescence protein (YFP) under the control of the plastidial Prrn promoter from tobacco for transient expression in the chloroplasts was employed. A near-infrared (NIR) image shows that the pDNA-SWNT assemblies were able to penetrate the protoplast and chloroplast membranes and are localized within the chloroplasts (FIG. 3C; FIG. 11). After a 24 h incubation of the isolated protoplasts with pDNA-$CS^{COV}$-SWNTs (3 mg L$^{-1}$; 1:6 pDNA:SWNT w/w ratio) at room temperature, transient YFP expression was observed in the chloroplasts in fluorescence confocal micrographs (FIG. 3D). No YFP expression was detected when protoplasts were incubated with only pDNA (FIG. 12A). The viability of protoplasts was compromised when incubated with non-covalently modified CS-SWNTs. This is consistent with the observation of poor colloidal stability of CS-SWNTs in high salt concentrations of MMG buffer solution, as free chitosan molecules were reported to cause protoplast agglutination through the formation of polycationic bridges between protoplasts. See, reference 58. The effect of the pDNA:SWNT ratio on chloroplast-targeted gene delivery efficiency was also investigated. When the mass ratio of pDNA:SWNT was increased to 1:1, no YFP expression was observed in the mesophyll chloroplasts using $CS^{COV}$-SWNT (FIG. 12B). Higher pDNA loading results in surface charge neutralization of the pDNA-SWNT conjugates, which causes both colloidal instability and lower driving force to penetrate through the chloroplast double lipid bilayers as postulated by our LEEP model (FIG. 2A-2D).

Figure 4A:
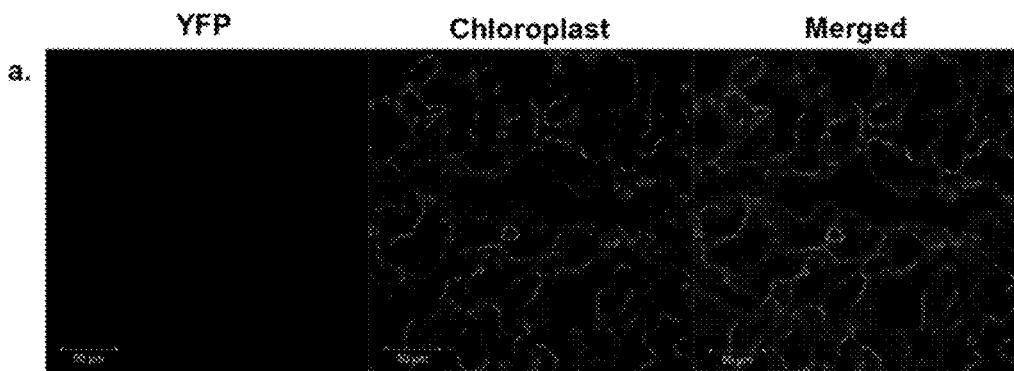
Figure 4B:
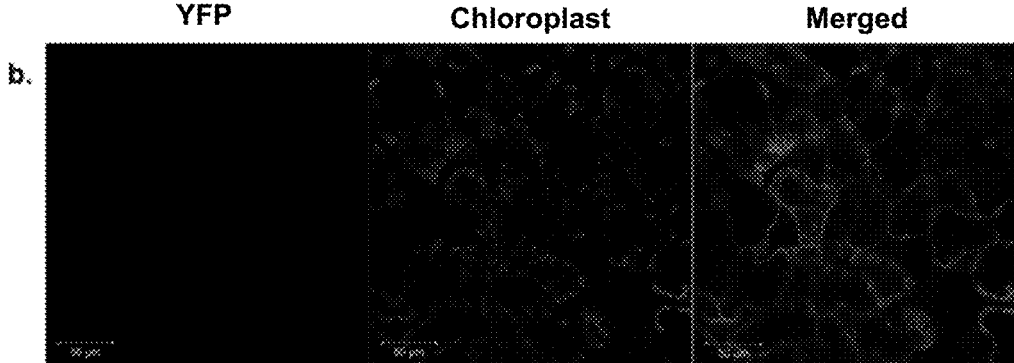
Figure 4C:
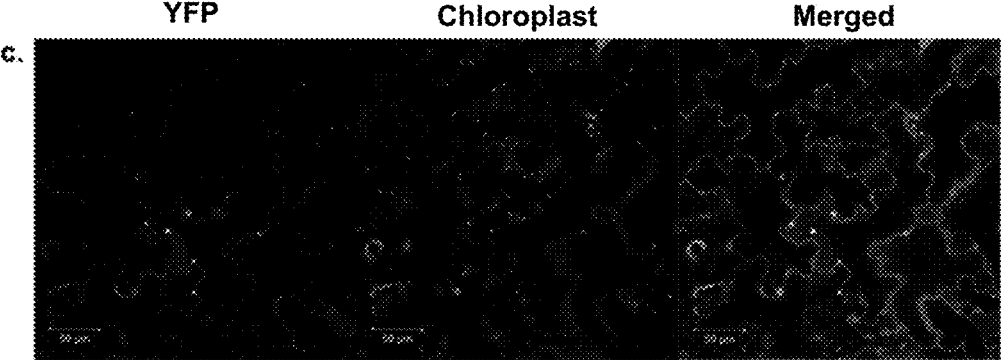
Figure 14A:
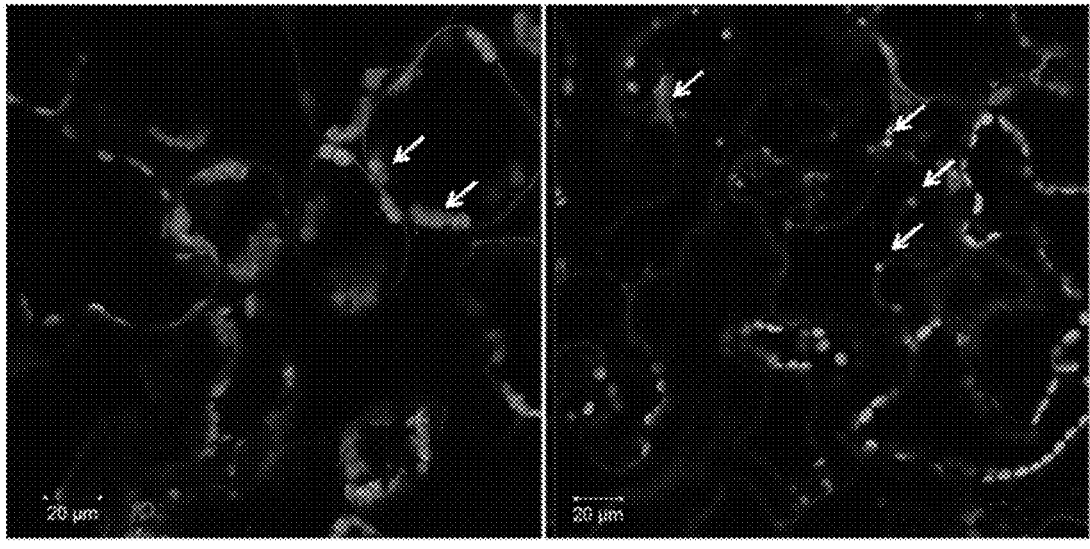
FIG. 14A-14B depict fluorescence confocal micrographs of the arugula leaves infiltrated with pDNA:$CS^{COV}$-SWNT conjugates (1.5 mg L$^{-1}$, pDNA:SWNT=1:3) after 3 days. A reduced YFP (yellow; white arrow) signal is observed in chloroplasts (cyan).
Figure 14B:
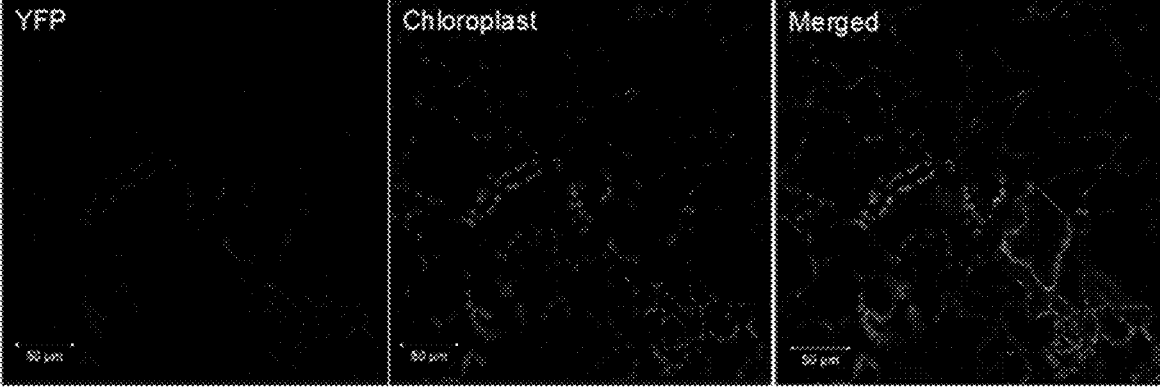

To ensure our chitosan-complexed SWNTs can function as selective DNA nanocarriers to target the chloroplasts in a living plant, pDNA-SWNT assemblies to the leaves of four-week-old mature arugula (Eruca sativa) plants by a localized infiltration method was infiltrated. See, reference 59. Previously, previously reported leaf infiltration with ss(AT)$_{15}$-SWNTs at 5 mg L$^{-1}$ did not affect the spinach leaf lifespan. See, reference 34. However, in arugula plants, it was found that chitosan-complexed SWNTs need to be applied below 2.5 mg L$^{-1}$ to avoid a detrimental effect on the leaf chlorophyll content, which indicates the onset of leaf senescence (FIGS. 13A-13B). Various experimental sets of pDNA-SWNT assemblies with SWNT concentration of 2.5 or 1.5 mg L$^{-1}$ and SWNT:pDNA ratio of 1:1, 3:1 or 6:1 (w/w) were prepared, followed by infusion of 50-100 µL of the nanocomplexes to the arugula leaves. Selective transient transgene expression was achieved in the chloroplasts with CS$^{COV}$-SWNTs (1.5 mg L$^{-1}$) at a SWNT:pDNA ratio of 3:1 (w/w) and CS$^{PEG5K}$-SWNTs (2.5 mg L$^{-1}$) at a SWNT:pDNA ratio of 6:1 (w/w) (FIGS. 4C-4E). The estimated efficiency of delivery of the pDNA cargo to the chloroplast and its subsequent transient expression is up to 47% for SWNT:pDNA ratio of 3:1 at 1.5 mg L$^{-1}$ concentration based on the confocal fluorescence micrographs. This passive transgene delivery and expression in the chloroplast was achieved by using only approximately 20 ng of pDNA, which is 1000 times less pDNA than that typically used for PEG-mediated protoplast transformation (20-50 µg) and 250 times less than the amount needed for biolistic plastid transformation (5 µg). See, references 60 and 61. The results further indicate that pDNA integrity is protected from cellular degradation when bound to chitosan-complexed SWNTs, as evidenced by the successful expression within the chloroplast, while traversing past the plant cell wall, plasma membrane and double lipid bilayers of chloroplast without the aid of biolistic force. The transient YFP expression reached the maximum after approximately 48 h from the infiltration of pDNA-SWNTs and decreased over time (FIG. 14A). It was also found that at 1.5 mg L$^{-1}$ SWNT, chloroplast transformation could be achieved at 1:3 pDNA:SWNT ratio but not at 1:6 ratio, possibly due to the low amount of pDNA transported into the chloroplast in the latter case (FIG. 14B).

Figure 15A:
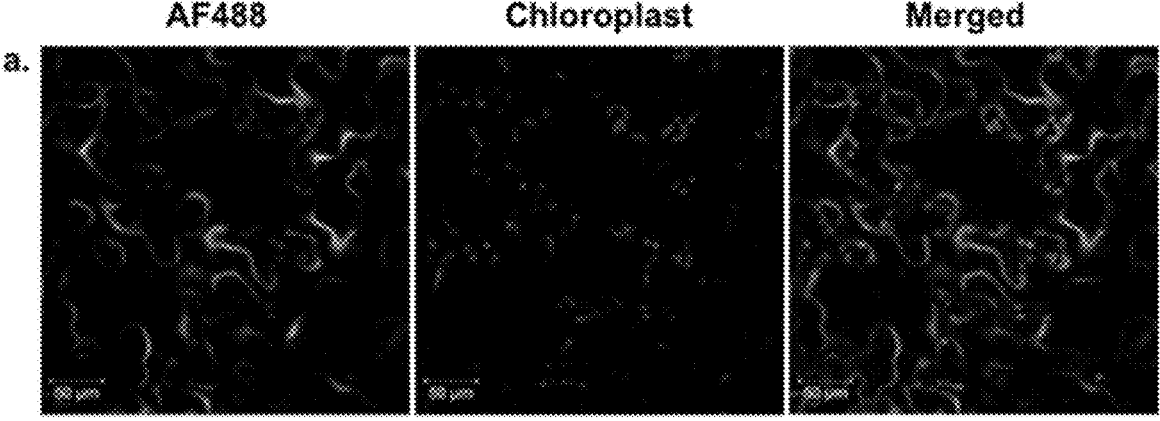
FIGS. 15A-15C depict the estimated co-localization efficiency of $CS^{COV}$-SWNTs in chloroplasts.
Figure 15B:
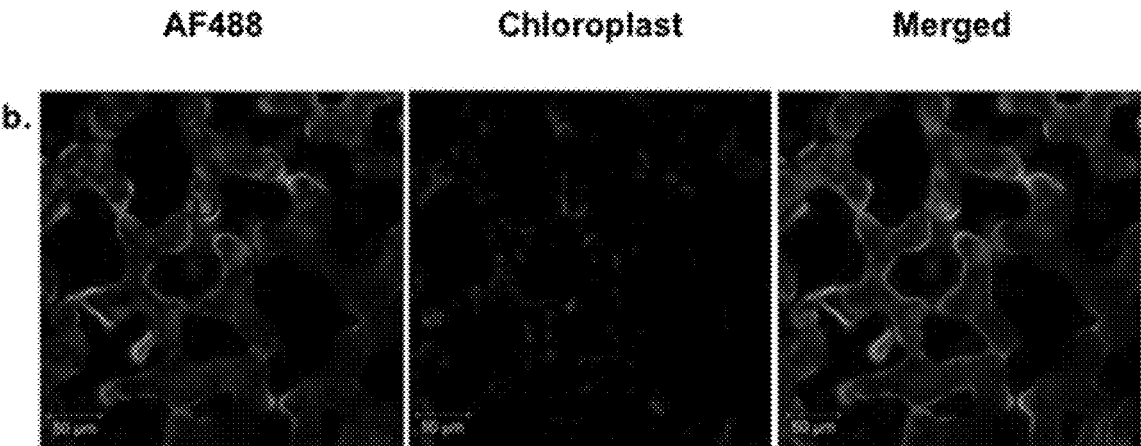
Figure 15C:
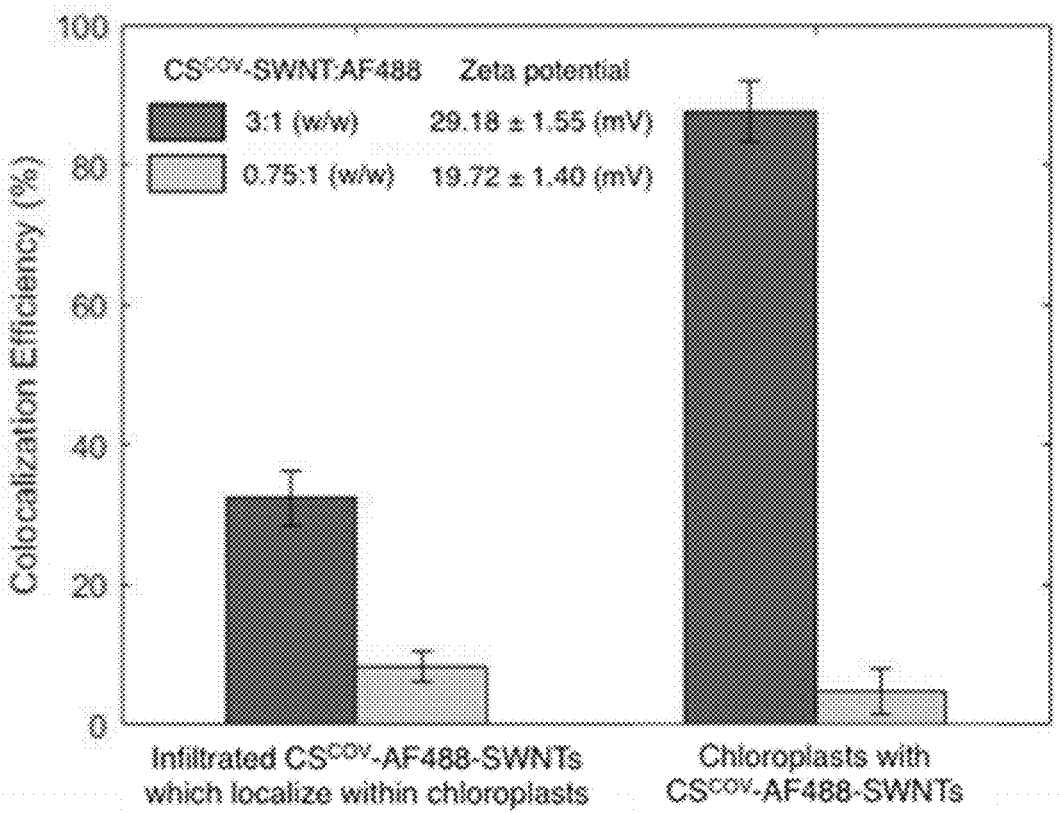

Using dye-labeled CS$^{COV}$-SWNT, with a SWNT:dye ratio of 3:1 (w/w), it was estimated that about 35% of the infiltrated SWNTs localized in the chloroplasts and 88% of the chloroplasts showed co-localization with dye-labeled SWNTs (FIG. 15). The zeta potential of this complex was measured to be +29.2 mV. On the other hand, when the SWNT:dye ratio was 3:4 (w/w), the zeta potential of the complex decreased to +19.7 mV and only 8% of the infiltrated SWNTs were localized in the chloroplasts, with only 3% of the chloroplasts showing SWNTs. This observation further confirms our LEEP model that zeta potential, and thus the ratio of pDNA:SWNT, influences the trafficking efficiency of the nanocomplexes into the chloroplasts. There is insignificant YFP expression in the leaves infiltrated with pDNA-CS-SWNT or pDNA-CS$^{PEG2}$K-SWNT assemblies, which could be attributed to the nanocomplexes' low colloidal stability in plant tissues or pre-mature release of pDNA prior to entering the chloroplasts. The non-covalent interaction energy between chitosan and carbon nanotube sidewall is estimated to be approximately 1.5 kcal/mol, which is far weaker than that of a C—C covalent bond strength in CS$^{COV}$-SWNTs (~88 kcal/mol). See, reference 62. In addition, CS$^{COV}$-SWNTs have a higher availability of free chitosan chains that can bind to the pDNA due to its more open architecture, whereas a larger proportion of the chitosan chain interacts with the side wall of SWNT in non-covalently functionalized chitosan-SWNTs. Thus the free amino group availability in these complexes is reduced due to steric hindrance (FIG. 1B). This contributes to CS$^{COV}$-SWNTs having a higher zeta potential than other chitosan-wrapped SWNTs (FIG. 2A). The higher zeta potential of CS$^{COV}$-SWNTs suggests that CS$^{COV}$-SWNTs can bind onto the anionic DNA molecules more tightly and deliver pDNA into the chloroplasts more safely after crossing all the biological barriers and membranes in plants. Once inside the chloroplasts, the basic pH environment within the stroma weakened the electrostatic binding between pDNA and amino groups of CS$^{COV}$-SWNT, releasing the pDNA and resulting in targeted pDNA delivery that leads to transient expression of YFP within the chloroplasts. It is proposed that the weaker interaction between chitosan and the SWNT surface in non-covalently modified CS-SWNTs and CS$^{PEG2K}$-SWNTs led to lower colloidal stability of these complexes within plant tissues, which may result in competitive binding from intrinsic plant biomolecules and early release of pDNA before they reach the chloroplasts. On the other hand, the use of CS$^{PEG5K}$-SWNTs as nanocarriers led to successful pDNA delivery and subsequent YFP expression in the chloroplasts (FIG. 4E). Such improvement in gene expression could be attributed to the enhanced stability of pDNA-SWNT assemblies when chitosan is conjugated with a longer PEG chain. No YFP expression was detected in control leaves infiltrated with 20 mM MES-MgCl$_2$ buffer or pDNA-chitosan conjugates with different pDNA:chitosan ratios from 1:1 to 1:10 (w/w) without SWNTs (FIGS. 4A and 4B).

Figure 16:
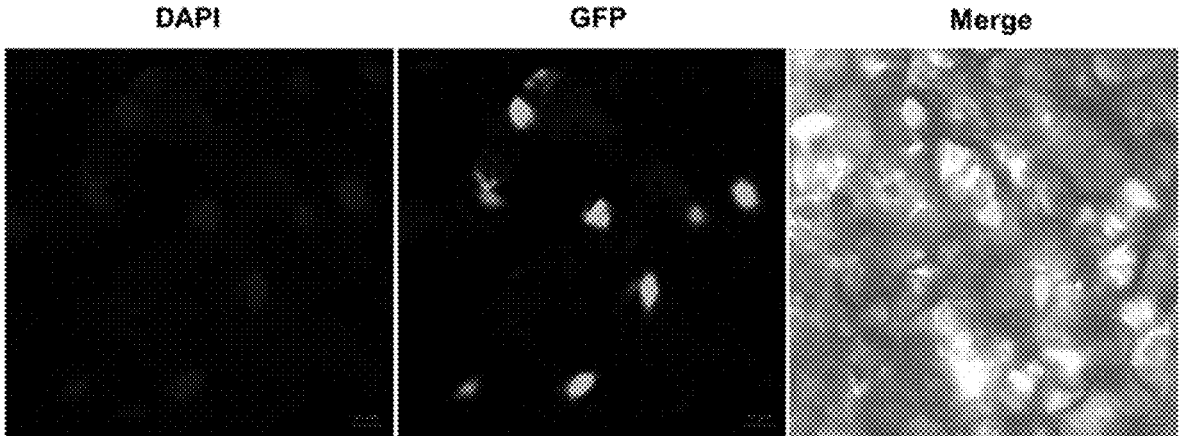
FIG. 16 *Agrobacterium*-mediated transformation in arugula leaf. *Agrobacterium* containing binary vector pBA-GFP-NLS (35S:GFP-NLS) was infiltrated into arugula leaf. DAPI was used for nucleus staining. Confocal images were taken 2 days after infiltration. Scale bars=10 μm.

In addition, a set of positive control experiments was carried out with pDNA-SWNT conjugates using pDNA designed for nuclear transformation with a green fluorescence protein (GFP) marker and a nuclear localization tag (pBA-GFP-NLS; see Examples). A positive control using *Agrobacterium tumefaciens* transformation confirmed that this reporter GFP pDNA can be transiently expressed in the nucleus of arugula mesophyll cells (FIG. 16). On the other hand, since the chitosan-functionalized SWNT carriers are designed to selectively release pDNA in the chloroplast stroma, no GFP expression was observed in the nucleus of the mesophyll cells when it was introduced via our nanoparticle-mediated approach (FIGS. 4F and 4G). This demonstrates that selective pDNA delivery to the chloroplast can be achieved by using chitosan-complexed SWNTs.

Figure 4H:
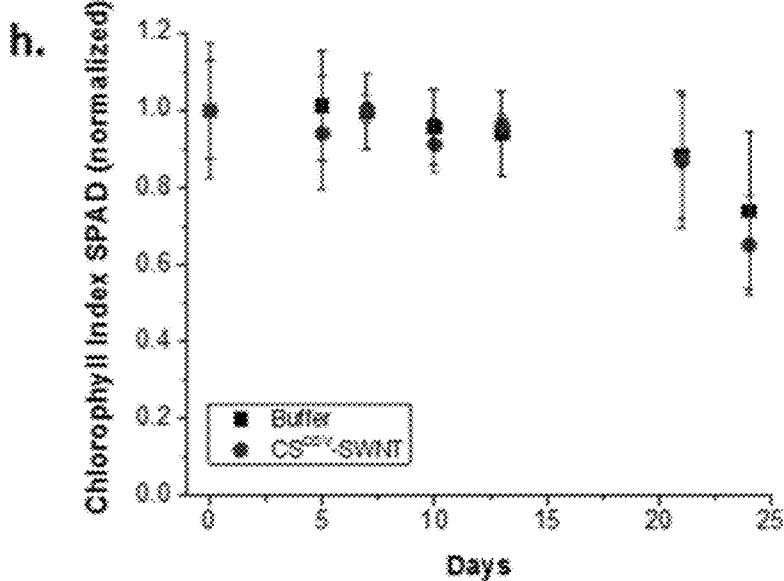

The effect of SWNT nanocarriers on the leaf lifespan by monitoring the chlorophyll content was further evaluated. Leaves of three-week-old arugula plants were infiltrated with CS$^{COV}$-SWNT (2.5 mg L$^{-1}$) or 20 mM MES-MgCl$_2$ buffer (control). Their chlorophyll content showed a similar temporal profile with no significant change in the chlorophyll content index for 3.5 weeks after infiltration, indicating that the leaf lifespan was not affected by chitosan-functionalized nanocarriers (FIG. 4H).

Figure 5A:
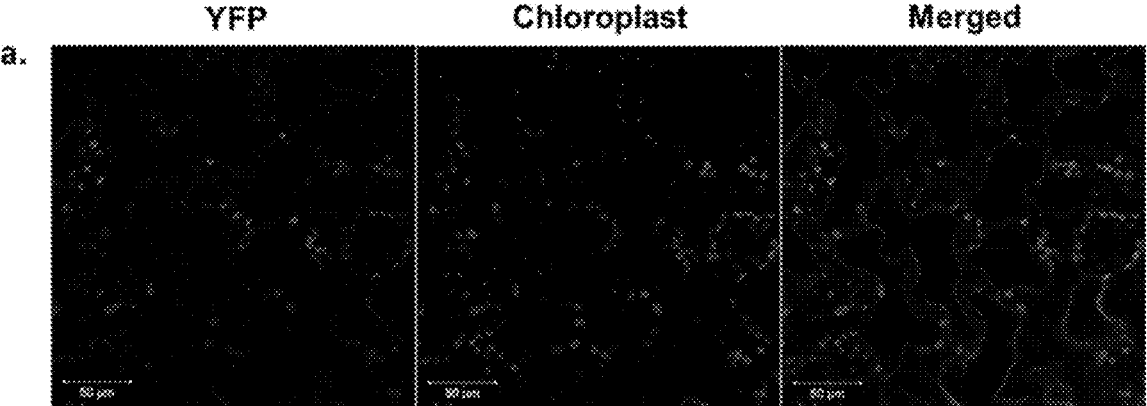
FIGS. 5A-5C depict chloroplast-targeted gene delivery and transient YFP expression in mature plants. Fluorescence confocal micrographs were taken after 2 or 3 days post-infiltration.
Figure 5B:
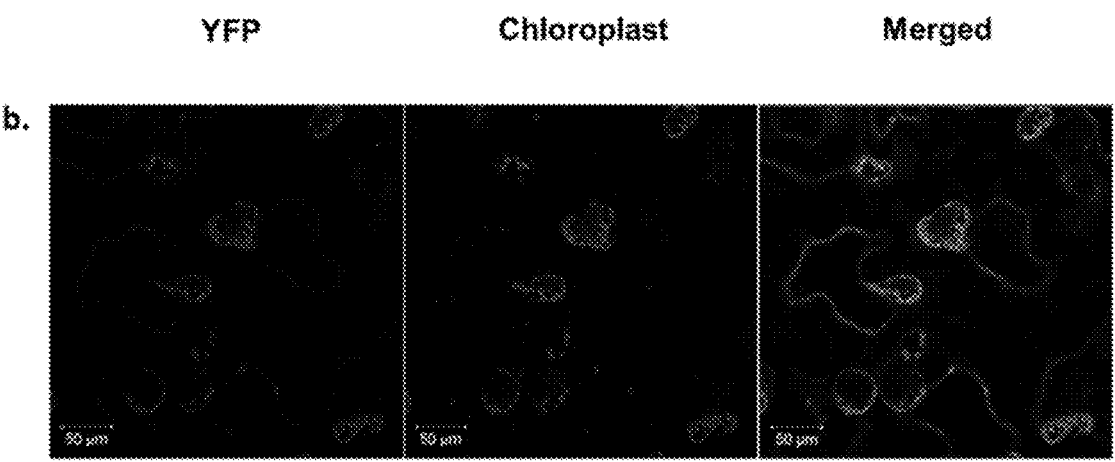
Figure 5C:
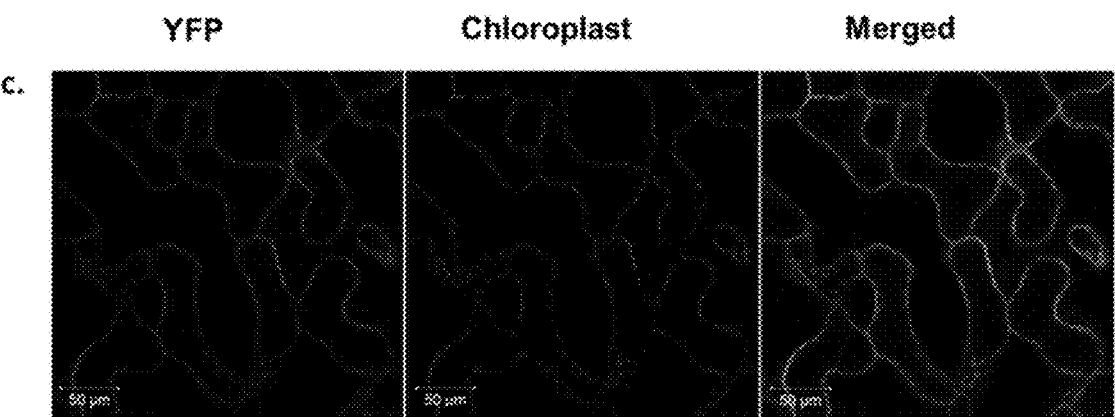

Finally, it was demonstrated that our nanoparticle-mediated delivery approach could also be applied to other plant species. To this end, pDNA-CS$^{COV}$-SWNT conjugates were infiltrated to the leaves of mature wild-type watercress (*Nasturtium officinale*), spinach (*Spinacia oleracea*) and tobacco (*Nicotiana benthamiana*) plants. Tobacco was of particular interest to us since it was the first higher plant species in which chloroplast transformation was successfully demonstrated and tobacco is commonly used for plastid transformation studies. See, references 63 and 64. Transient YFP expression in the chloroplasts of watercress plants was observed 2 and 3 days after infiltration of CS$^{COV}$-SWNTs (2.5 mg L$^{-1}$) at a pDNA:SWNT ratio of 1:6 (w/w) (FIG. 5A). The estimated efficiency of pDNA delivery and subsequent transient expression in the chloroplast is up to 65% at the 3$^{rd}$ day based on the confocal fluorescence micrographs. YFP expression was also observed in the chloroplasts of mature spinach and tobacco leaves 3 days post-infiltration (FIGS. 5B and 5C). It was noted that the optimum concentration of nanocarriers and the corresponding pDNA nanocomplexes that can be infiltrated to the leaf lamina would need to be optimized across different species depending on their leaf histology and surface properties. For example, to achieve successful gene delivery to the chloroplasts, the optimum $CS^{COV}$-SWNTs concentration for arugula and tobacco was found to be 1.5 mg $L^{-1}$, while the optimum nanocarrier concentration for spinach and watercress was determined to be 2.5 mg $L^{-1}$. The applicability of the nanoparticles-mediated delivery platform in these species suggests that chitosan-complexed SWNTs can serve as promising nanocarriers for targeted transgene delivery and expression across a broad range of plant species, without the aid of external force.

In this study, the possibility of chloroplast transformation using chitosan-complexed SWNT as nanocarriers was demonstrated. Four types of chitosan-based positively charged SWNT carriers were prepared to protect and deliver pDNA to the chloroplasts and validated the unloading mechanism of pDNA in the weakly basic environment of pH 8, which mimics the biological environment within the chloroplast stroma. These chitosan-functionalized SWNT complexes were rationally designed using the LEEP model can maximize the trafficking efficiency of the SWNT conjugates into the plant chloroplasts. By using a pDNA encoding a YFP reporter gene, chloroplast-targeted gene delivery and transgene expression was demonstrated in mature arugula, watercress, spinach and tobacco plants as well as in isolated *Arabidopsis thaliana* mesophyll protoplasts. This selective nanoparticle-mediated chloroplast transgene delivery platform is simple, easy to perform, cost-effective, can be applied to mature plants across different species and does not require specialized, expensive equipment, enabling its widespread applications in plant bioengineering and plant biology studies. The presented approach permits facile conjugation chemistries and can potentially be extended to carry other biomolecular cargo, such as zinc finger nuclease, TALENs and CRISPR/Cas9 vectors for precise chloroplast genome editing applications in plants. Based on the initial results presented here, the developed platform could also be optimized further to enable stable chloroplast transformation in crop species to benefit crop improvement and agronomic applications. With the multiple rounds of selection and breeding that occur during line development for commercial crops, there should not be any trace of SWNTs present in the lines suggesting the nanoparticle-mediated transformation could be a commercially viable approach for crop transformation. Further studies may be required to ensure both the safe use and acceptability of this new genetic engineering tool for agricultural applications.

As used herein, the term "nanoparticle" refers to articles having at least one cross-sectional dimension of less than about 1 micron. A nanoparticle can also be referred to as a "nanostructure." A nanoparticle can have at least one cross-sectional dimension of less than about 500 nm, less than about 250 nm, less than about 100 nm, less than about 75 nm, less than about 50 nm, less than about 25 nm, less than about 10 nm, or, in some cases, less than about 1 nm. Examples of nanoparticle include nanotubes (e.g., carbon nanotubes), nanowires (e.g., carbon nanowires), graphene, and quantum dots, among others. In some embodiments, the nanoparticle can include a fused network of atomic rings, the atomic rings comprising a plurality of double bonds.

A nanoparticle can be a photoluminescent nanoparticle. A "photoluminescent nanoparticle," as used herein, refers to a class of nanoparticles that are capable of exhibiting photoluminescence. In some cases, photoluminescent nanoparticles can exhibit fluorescence. In some instances, photoluminescent nanoparticles exhibit phosphorescence. Examples of photoluminescent nanoparticles suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, and graphene, among others.

A variety of nanoparticles can be used. Sometimes a nanoparticle can be a carbon-based nanoparticle. As used herein, a "carbon-based nanoparticle" can include a fused network of aromatic rings wherein the nanoparticle includes primarily carbon atoms. In some instances, a nanoparticle can have a cylindrical, pseudo-cylindrical, or horn shape. A carbon-based nanoparticle can include a fused network of at least about 10, at least about 50, at least about 100, at least about 1000, at least about 10,000, or, in some cases, at least about 100,000 aromatic rings. A carbon-based nanoparticle may be substantially planar or substantially non-planar, or may include a planar or non-planar portion. A carbon-based nanoparticle may optionally include a border at which the fused network terminates. For example, a sheet of graphene includes a planar carbon-containing molecule including a border at which the fused network terminates, while a carbon nanotube includes a non-planar carbon-based nanoparticle with borders at either end. In some cases, the border may be substituted with hydrogen atoms. In some cases, the border may be substituted with groups comprising oxygen atoms (e.g., hydroxyl).

In some embodiments, a nanoparticle can include or be a nanotube. The term "nanotube" is given its ordinary meaning in the art and can refer to a substantially cylindrical molecule or nanoparticle including a fused network of primarily six-membered rings (e.g., six-membered aromatic rings). In some cases, a nanotube can resemble a sheet of graphite formed into a seamless cylindrical structure. It should be understood that a nanotube may also include rings or lattice structures other than six-membered rings. Typically, at least one end of the nanotube may be capped, i.e., with a curved or non-planar aromatic group. A nanotube may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may include a carbon nanotube. The term "carbon nanotube" can refer to a nanotube including primarily carbon atoms. Examples of carbon nanotubes can include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, a carbon nanotube can be a single-walled carbon nanotube. In some cases, a carbon nanotube can be a multi-walled carbon nanotube (e.g., a double-walled carbon nanotube).

In some embodiments, a nanoparticle can include non-carbon nanoparticles, specifically, non-carbon nanotubes. Non-carbon nanotubes may be of any of the shapes and dimensions outlined above with respect to carbon nanotubes. A non-carbon nanotube material may be selected from polymer, ceramic, metal and other suitable materials. For example, a non-carbon nanotube may include a metal such as Co, Fe, Ni, Mo, Cu, Au, Ag, Pt, Pd, Al, Zn, or alloys of these metals, among others. In some instances, a non-carbon nanotube may be formed of a semi-conductor such as, for example, Si. In some cases, a non-carbon nanotube may include a Group II-VI nanotube, wherein Group II includes Zn, Cd, and Hg, and Group VI includes O, S, Se, Te, and Po. In some embodiments, a non-carbon nanotube may include a Group III-V nanotube, wherein Group III includes B, Al, Ga, In, and Tl, and Group V includes N, P, As, Sb, and Bi. As a specific example, a non-carbon nanotube may include a boron-nitride nanotube. In other embodiments, the nanoparticle can be a ceramic, for example, a metal oxide, metal nitride, metal boride, metal phosphide, or metal carbide. In this example, the metal can be any metal, including Group I metal, Group II metal, Group III metal, Group IV metal, transition metal, lanthanide metal or actinide metal. For example, the ceramic can include one or more of metal, for example, Li, Na, K, Rb, Cs, Be, Mg, Ca, Sr, Ba, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, Su, Zn, Cd, Hg, Al, Ga, In, Tl, Si, Ge, Sn, Pb or Bi.

In some embodiments, a nanotube may include both carbon and another material. For example, in some cases, a multi-walled nanotube may include at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and can refer to semiconducting nanoparticles that exhibit quantum confinement effects. Generally, energy (e.g., light) incident upon a quantum dot can excite the quantum dot to an excited state, after which, the quantum dot can emit energy corresponding to the energy band gap between its excited state and its ground state. Examples of materials from which quantum dots can be made include PbS, PbSe, CdS, CdSe, ZnS, and ZnSe, among others.

A photoluminescent nanoparticle can be, in some cases, substantially free of dopants, impurities, or other non-nanoparticle atoms. For example, in some embodiments, a nanoparticle can include a carbon nanoparticle that is substantially free of dopants. As a specific example, in some embodiments, a nanoparticle can include single-walled carbon nanotube that contains only aromatic rings (each of which contains only carbon atoms) within the shell portion of the nanotube. In other words, a nanoparticle can consist essentially of a single material, for example, carbon.

In some embodiments, a photoluminescent nanoparticle may emit radiation within a desired range of wavelengths. For example, in some cases, a photoluminescent nanoparticle may emit radiation with a wavelength between about 750 nm and about 1600 nm, or between about 900 nm and about 1400 nm (e.g., in the near-infrared range of wavelengths). In some embodiments, a photoluminescent nanoparticle may emit radiation with a wavelength within the visible range of the spectrum (e.g., between about 400 nm and about 700 nm).

In some embodiments, a photoluminescent nanoparticle may be substantially free of covalent bonds with other entities (e.g., other nanoparticles, a current collector, the surface of a container, a polymer, an analyte, etc.). The absence of covalent bonding between a photoluminescent nanoparticle and another entity may, for example, preserve the photoluminescent character of the nanoparticle. In some cases, single-walled carbon nanotubes or other photoluminescent nanoparticles may exhibit modified or substantially no fluorescence upon forming a covalent bond with another entity (e.g., another nanoparticle, a current collector, a surface of a container, and the like).

In some embodiments, a nanoparticle can include cerium oxide. A nanoparticle including cerium oxide can be referred to as nanoceria. A nanoparticle can be cerium oxide. A nanoparticle can also be conjugated to at least one cerium oxide nanoparticle. Conjugation can be direct or indirect. Conjugation can also be through a covalent bond, ionic bond or van der Waals interaction. A nanoparticle can be cross-linked with at least one cerium oxide nanoparticle, more specifically, cross-linked using via carbodiimide chemistry. In one example, a carbodiimide agent N-ethyl-N'-(3-dimethylaminopropyl) carbodiimide hydrochloride (EDAC) can be used.

A nanoparticle can be strongly cationic or anionic. Strongly cationic or anionic can mean that the nanoparticle (or other element) has a high magnitude of the zeta potential. For example, the nanoparticle can have a zeta potential of less than −10 mV or greater than 10 mV. In preferred embodiments, the nanoparticle can have a zeta potential of less than −20 mV or greater than 20 mV, a zeta potential of less than −30 mV or greater than 30 mV, or a zeta potential of less than −40 mV or greater than 40 mV.

A nanoparticle can include a coating or be suspended in a coating with a high magnitude of the zeta potential. A coating can be a polymer. A variety of polymers may be used in association with the embodiments described herein. In some cases, the polymer may be a polypeptide. In some embodiments, the length and/or weight of the polypeptide may fall within a specific range. For example, the polypeptide may include, in some embodiments, between about 5 and about 50, or between about 5 and about 30 amino acid residues. In some cases, the polypeptide may have a molecular weight of between about 400 g/mol and about 10,000 g/mol, or between about 400 g/mol and about 600 g/mol. Examples of protein polymers can include glucose oxidase, bovine serum albumin and alcohol dehydrogenase.

A polymer may include a linear or branched synthetic polymer (e.g., polybrene, polyethyleneimine, poly(ethylene oxide), poly(vinyl pyrrolidinone), poly(allyl amine), poly(2-vinylpyridine), and the like), in some embodiments.

A polymer may include a natural polymer, for example, histone and collagen, in some embodiments.

In some embodiments, the polymer may include an oligonucleotide. The oligonucleotide can be, in some cases, a single-stranded DNA oligonucleotide. The single-stranded DNA oligonucleotide can, in some cases, include a majority (>50%) A or T nucleobases. In some embodiments, single-stranded DNA oligonucleotide can include more than 75%, more than 80%, more than 90%, or more than 95% A or T nucleobases. In some embodiments, the single-stranded DNA oligonucleotide can include a repeat of A and T. For example, a oligonucleotide can be, in some cases, at least 5, at least 10, at least 15, between 5 and 25, between 5 and 15, or between 5 and 10 repeating units, in succession, of (GT) or (AT). Repeating units can include at least 2 nucleobases, at least 3 nucleobases, at least 4 nucleobases, at least 5 nucleotides long. The nucleobases described herein are given their standard one-letter abbreviations: cytosine (C), guanine (G), adenine (A), and thymine (T).

In some embodiments, the polymer can include a polysaccharide such as, for example, cyclodextran, pectin, hyaluronic acid, hydroxyethylcellulose, amylose, chitosan, or chitin.

In some embodiments, the polymer can include an oligopeptide or a polypeptide, for example, polylysine, polyhistidine, polyornithine or polyarginine.

In preferred embodiments, the interaction between a polymer and a nanoparticle can be non-covalent (e.g., via van der Waals interactions); however, a polymer can covalently bond with a nanoparticle. In some embodiments, the polymer may be capable of participating in a pi-pi interaction with the nanostructure. A pi-pi interaction (a.k.a., "pi-pi stacking") is a phenomenon known to those of ordinary skill in the art, and generally refers to a stacked arrangement of molecules adopted due to interatomic interactions. Pi-pi interactions can occur, for example, between two aromatic molecules. If the polymer includes relatively large groups, pi-pi interaction can be reduced or eliminated due to steric hindrance. Hence, in certain embodiments, the polymer may be selected or altered such that steric hindrance does not inhibit or prevent pi-pi interactions. One of ordinary skill in the art can determine whether a polymer is capable or participating in pi-pi interactions with a nanostructure.

The polymer complexed nanoparticles may be strongly cationic or anionic, meaning that the polymer has a high magnitude of the zeta potential. For example, the polymer can have a zeta potential of less than −10 mV or greater than 10 mV, less than −20 mV or greater than 20 mV, less than −30 mV or greater than 30 mV, or less than −40 mV or greater than 40 mV.

A nanoparticle can be contained within a chloroplast, as demonstrated more fully herein. A nanoparticle can traverse and/or localize within the outer membrane layer (i.e., lipid bilayer). The process can be complete and/or irreversible. Because other organelles include an outer membrane layer (i.e., lipid bilayer), a nanoparticle can be contained within other organelles. For example, other organelles that a nanoparticle can be introduced into can include a nucleus, endoplasmic reticulum, Golgi apparatus, chloroplast, chromoplast, gerontoplast, leucoplast, lysosome, peroxisome, glyoxysome, endosome, mitochondria or vacuole.

Thylakoids are a membrane-bound compartment inside a chloroplast. Cyanobacteria can also include thylakoids. In some embodiments, a nanoparticle can be associated with a thylakoid membrane within a chloroplast, cyanobacteria or other photocatalytic cell or organelle.

A nanoparticle can be contained within a photocatalytic unit, most preferably, including an outer lipid membrane (i.e., lipid bilayer). A photocatalytic unit can be a structure capable of performing photosynthesis or photocatalysis, preferably a cell or an organelle capable of performing photosynthesis or photocatalysis. For example, a photocatalytic unit can be a chloroplast, a cyanobacteria, or a bacterial species selected from the group consisting of *Chlorobiacea* spp., a *Chromaticacea* spp. and a *Rhodospirillacae* spp.

An organelle can be part of a cell, a cell can be part of a tissue, and a tissue can be part of an organism. For example, a nanoparticle can be contained within a cell of a leaf of a plant. More to the point, a cell can be intact. In other words, the organelle may not be an isolated organelle, but rather, the organelle can be contained within the outer lipid membrane of a cell.

A nanoparticle that is independent of an organelle or cell can be free of lipids. An outer lipid membrane can enclose or encompass an organelle or cell. As the nanoparticle traverses the outer lipid membrane of an organelle or cell, lipids from the outer lipid membrane can associate or coat the nanoparticle. As a result, a nanoparticle inside the outer lipid membrane of an organelle or cell can be associated with or coated with lipids that originated in the organelle or cell.

Transport of a nanoparticle into an organelle or a cell can be a passive process. In some cases, transport across the outer lipid membrane can be independent of the temperature or light conditions.

Embedding a nanoparticle within an organelle or cell can be useful for monitoring the activity of the organelle or cell. For example, a nanoparticle, preferably a photoluminescent nanoparticle, can be introduced into the organelle or cell. Measurements of the photoluminescence of a photoluminescent nanoparticle can provide information regarding a stimulus within an organelle or cell. Measurements of the photoluminescence of a photoluminescent nanoparticle can be taken at a plurality of time points. A change in the photoluminescence emission between a first time point and a second time point can indicate a change in a stimulus within the organelle or cell.

In some embodiments, a change in the photoluminescence emission can include a change in the photoluminescence intensity, a change in an emission peak width, a change in an emission peak wavelength, a Raman shift, or combination thereof. One of ordinary skill in the art would be capable of calculating the overall intensity by, for example, taking the sum of the intensities of the emissions over a range of wavelengths emitted by a nanoparticle. In some cases, a nanoparticle may have a first overall intensity, and a second, lower overall intensity when a stimulus changes within the organelle or cell. In some cases, a nanoparticle may emit a first emission of a first overall intensity, and a second emission of a second overall intensity that is different from the first overall intensity (e.g., larger, smaller) when a stimulus changes within the organelle or cell.

A nanoparticle may, in some cases, emit an emission of radiation with one or more distinguishable peaks. One of ordinary skill in the art would understand a peak to refer to a local maximum in the intensity of the electromagnetic radiation, for example, when viewed as a plot of intensity as a function of wavelength. In some embodiments, a nanoparticle may emit electromagnetic radiation with a specific set of peaks. In some cases, a change in a stimulus may cause the nanoparticle to emit electromagnetic radiation including one or more peaks such that the peaks (e.g., the frequencies of the peaks, the intensity of the peaks) may be distinguishable from one or more peaks prior to the change in stimulus. In some cases, the change in a stimulus may cause the nanoparticle to emit electromagnetic radiation comprising one or more peaks such that peaks (e.g., the frequencies of the peaks, the intensity of the peaks) are distinguishable from the one or more peaks observed prior to the change in the stimulus. When the stimulus is the concentration of an analyte, the frequencies and/or intensities of the peaks may, in some instances, allow one to determine the analyte interacting with the nanoparticle by, for example, producing a signature that is unique to a particular analyte that is interacting with the nanoparticle. Determination of a specific analyte can be accomplished, for example, by comparing the properties of the peaks emitted in the presence of the analyte to a set of data (e.g., a library of peak data for a predetermined list of analytes).

A stimulus can include the pH of the organelle or cell. A change in the pH can be an increase or decrease in the pH.

A stimulus can include a modification of an analyte. For example, an analyte may be oxidized or reduced. In other examples, an analyte can be ionized. In another example, an analyte can include an ether, ester, acyl, or disulfide or other derivative.

A stimulus can include the concentration of an analyte. An analyte can include a reactive oxygen species, for example, hydrogen peroxide, superoxide, nitric oxide, and a peroxidase. Alternatively, an analyte can be carbon dioxide, adenosine triphosphate (ATP), nicotinamide adenine dinucleotide phosphate (NADP⁺ or NADPH), or oxygen. In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte). In some cases, the concentration of an analyte may be zero, indicating that no analyte is present.

Chloroplasts can be considered a high source of chemical energy in food supplies and carbon-based fuels on the planet. By capturing atmospheric $CO_2$, these plant organelles convert light energy into three major forms of sugars that fuel plant growth: maltose, triose phosphate and glucose. (Weise, S. E., Weber, A. P. M. & Sharkey, T. D. Maltose is the major form of carbon exported from the chloroplast at night. *Planta* 218, 474-82 (2004), which is incorporated by reference in its entirety). While some information exists on the interface between photosystems and nanomaterials, nanoengineering chloroplast photosynthesis for enhancing solar energy harnessing remains unexplored. (Boghossian, A. A. et al. Application of Nanoparticle Antioxidants to Enable Hyperstable Chloroplasts for Solar Energy Harvesting. *Adv. Energy Mater.* 3:7, p. 881-893 (2013), which is incorporated by reference in its entirety). One deterrent in using chloroplast photosynthetic power as an alternative energy source can be that these organelles are no longer independently living organisms. However, isolated chloroplasts from the algae *Vaucheria litorea* in symbiotic association with the sea slug *Elysia chlorotica* remarkably can remain functional for at least 9 months. (Trench, R. K., Boyle, J. E. & Smith, D. C. The Association between Chloroplasts of Codium fragile and the Mollusc *Elysia viridis*. I. Characteristics of Isolated Codium Chloroplasts. *Proc. R. Soc. B Biol. Sci.* 184, 51-61 (1973); and Rumpho, M. E., Summer, E. J. & Manhart, J. R. Solar-Powered Sea Slugs. Mollusc/Algal Chloroplast Symbiosis. 123, 29-38 (2000), each of which is incorporated by reference in its entirety). Land plant chloroplast photosystem activity can decline within a day after extraction, while ex vivo sugar output can last for only a few hours. (Weise, S. E., et al. (2004); Choe, H. & Thimann, K. The Senescence of Isolated Chloroplasts. *Planta* 121, 201-203 (1974); Green, B. J., Fox, T. C. & Rumpho, M. E. Stability of isolated algal chloroplasts that participate in a unique mollus/kleptoplast association. *Symbiosis* 40, 31-40 (2005); and Neuhaus, H. E. & Schulte, N. Starch degradation in chloroplasts isolated from C3 or CAM (crassulacean acid metabolism)-induced *Mesembryanthemum crystallinum* L. *Biochem. J.* 318, 945-53 (1996), each of which is incorporated by reference in its entirety). Although chloroplasts have mechanisms in place to self-repair photo-damaged proteins, a double-stranded circular DNA with a subset of protein-encoding genes involved in photosynthesis, and ribosomal units for protein synthesis and assembly, little is known about engineering these plant organelles for long-term, stable photosynthesis ex vivo. (Edelman, M. & Mattoo, A. K. D1-protein dynamics in photosystem II: the lingering enigma. *Photosynth. Res.* 98, 609-20 (2008); Schmitz-Linneweber, C. et al. The plastid chromosome of spinach (*Spinacia oleracea*): complete nucleotide sequence and gene organization. *Plant Mol. Biol.* 45, 307-15 (2001); and Marín-Navarro, J., Manuell, A. L., Wu, J. & P Mayfield, S. Chloroplast translation regulation. *Photosynth. Res.* 94, 359-74 (2007), each of which is incorporated by reference in its entirety). Another limitation of chloroplasts photosynthesis can be that absorbed light is constrained to the visible range of the spectrum, allowing access to only roughly 50% of the incident solar energy radiation. (Bolton, J. R. & Hall, D. Photochemical conversion and storage of solar energy. *Annu. Rev. Energy* 4, 353-401 (1979), which is incorporated by reference in its entirety). Furthermore, in some conditions, less than 10% of full sunlight saturates the capacity of the photosynthetic apparatus. (Zhu, X.-G., Long, S. P. & Ort, D. R. Improving photosynthetic efficiency for greater yield. *Annu. Rev. Plant Biol.* 61, 235-61 (2010), which is incorporated by reference in its entirety). Photosynthetic organisms appear to have evolved for reproductive success, including shading competitors, not for solar energy conversion efficiency. Thus improving photosynthetic efficiency may require extending the range of solar light absorption, particularly in the near infrared spectral range, which is able to penetrate deeper into living organisms. (Blankenship, R. E. et al. Comparing photosynthetic and photovoltaic efficiencies and recognizing the potential for improvement. *Science* 332, 805-9 (2011), which is incorporated by reference in its entirety).

The high stability and unique chemical and physical traits of nanomaterials have the potential to enable chloroplast-based photocatalytic complexes both ex vivo and in vivo with enhanced and novel functional properties. Single-walled carbon nanotubes ("SWNTs") embedded within chloroplasts have the potential to enhance the light reactions of photosynthesis with their distinctive optical and electronic properties. Under bright sunlight, chloroplast photosystems can capture more photons than they can convert into electron flow. (Wilhelm, C. & Selmar, D. Energy dissipation is an essential mechanism to sustain the viability of plants: The physiological limits of improved photosynthesis. *J. Plant Physiol.* 168, 79-87 (2011), which is incorporated by reference in its entirety). However, under non-saturating light conditions, maximizing solar energy capture can be crucial. (Scholes, G. D., Fleming, G. R., Olaya-Castro, A. & van Grondelle, R. Lessons from nature about solar light harvesting. *Nat. Chem.* 3, 763-774 (2011), which is incorporated by reference in its entirety). SWNTs can absorb light over a broad range of wavelengths in the ultraviolet, visible and nIR spectra not captured by the chloroplast antenna pigments (FIGS. 49 and 53). The electronic band gap of semiconducting SWNTs can allow them to convert this absorbed solar energy into excitons that could transfer electrons to the photosynthetic machinery. (Han, J.-H. et al. Exciton antennas and concentrators from core-shell and corrugated carbon nanotube filaments of homogeneous composition. *Nat. Mater.* 9, 833-9 (2010), which is incorporated by reference in its entirety). Also, SWNT-based nanosensors can monitor single-molecule dynamics of free radicals within chloroplasts for optimizing photosynthetic environmental conditions (light and $CO_2$). (Zhang, J. et al. Single Molecule Detection of Nitric Oxide Enabled by d(AT)(15) DNA Adsorbed to Near Infrared Fluorescent Single-Walled Carbon Nanotubes. *J. Am. Chem. Soc.* 20, 567-581 (2010), which is incorporated by reference in its entirety). However, nanoengineering photosynthesis can require the delivery of nanomaterials through the chloroplast outer envelope. Nanoparticle transport through lipid bilayers has been described to be energy dependent, requiring endocytosis pathways that have not been reported in isolated chloroplasts. (Shi, X., von dem Bussche, A., Hurt, R. H., Kane, A. B. & Gao, H. Cell entry of one-dimensional nanomaterials occurs by tip recognition and rotation. *Nat. Nanotechnol.* 6, 714-9 (2011), which is incorporated by reference in its entirety). To date, nanomaterial uptake mechanisms through cell membranes are controversial and poorly understood in organelles like chloroplasts. (Pogodin, S., Slater, N. K. H. & Baulin, V. a. Surface patterning of carbon nanotubes can enhance their penetration through a phospholipid bilayer. *ACS Nano* 5, 1141-6 (2011), which is incorporated by reference in its entirety).

The interface between plant organelles and non-biological nanoparticles has the potential to impart the former with new and enhanced functions. For example, this nanobionic approach can yield chloroplasts that possess enhanced photosynthetic activity both ex vivo and in vivo, are more stable to reactive oxygen species ex vivo, and allow real time information exchange via embedded nanosensors for free radicals in plants. Accordingly, there is a need for nanoparticles that can interface with organelles, specifically, plant organelles ex vivo and in vivo to enable novel or enhanced functions. Similarly, there is a need for nanoparticles that can interface with intact photosynthetic organisms or intact cells of photosynthetic organisms ex vivo and in vivo to enable novel or enhanced functions. For example, the assembly of nanoparticle complexes within chloroplast photosynthetic machinery has the potential to enhance solar energy conversion through augmented light reactions of photosynthesis and ROS scavenging while imparting novel sensing capabilities to living plants.

Examples

Low molecular weight chitosan (5 g) was first added to 50 mL of 40% (w/v) sodium hydroxide and the deacetylation proceeded for 8 h at 90° C. under $N_2$. The resulting mixture was washed with deionized water multiple times until the supernatant reached a neutral pH, and was then dried in vacuum. The deacetylated chitosan was dissolved in 0.3% acetic acid and mixed with Raw HiPCO (Unidym, 0.8-1.2 nm in diameter with 1 nm mean diameter and 100 nm-1 μm initial length) in 2:1 (w/w) ratio. The mixture was tip-sonicated with 6-mm probe tip at 40% amplitude for 40 min in an ice bath. The resulting chitosan wrapped SWNT suspension (CS-SWNT) was dialyzed overnight against deionized water with dialysis membranes of 100 kDa MWCO to remove acetic acid as well as some of the free chitosan. CS-SWNT is purified by ultracentrifugation at 36,500 rpm at 15° C. for 4 h to remove bundles. For PEGylated chitosan wrapped SWNT, CS-SWNT suspension is mixed with 0.1 equiv. of PEG-NHS (Mw. 2000 or 5000, Aldrich) for 6 h at room temperature, then dialyzed overnight to remove free PEG chains and chitosan. PEGylated chitosan wrapped SWNT ($CS^{PEG2K}$-SWNT, $CS^{PEG5K}$-SWNT) is centrifuged at 16,100 g at 15° C. for 1.5 h to remove aggregates. Covalently bonded chitosan SWNTs ($CS^{COV}$-SWNT) were prepared by conjugation of carboxylated SWNTs (Sigma Aldrich) to the amino groups of chitosan by amide coupling chemistry using N-ethyl-N'-(3-dimethylaminopropyl)-carbodiimide (EDC) and N-hydroxysulfo-succinimide (Sulfo-NHS). 50 mg of chitosan dissolved in 0.3% (v/v) acetic acid aqueous solution was reacted with 5 mg carboxylated SWNTs suspension (1 mg $mL^{-1}$). EDC and Sulfo-NHS were used as coupling reagents at 5 mg $mL^{-1}$ concentration. Both mixtures were bath sonicated for 5 minutes, and subsequently stirred for 16 h at 30° C. The reaction mixtures were subsequently cooled to room temperature and tip-sonicated with 6-mm probe tip at 40% amplitude for 45 minutes in an ice bath. The resulting solutions were dialyzed for 3 days against deionized water with dialysis membranes of 100 kDa MWCO to remove excess reactants, then centrifuged at 16,100 g for 1 h to remove SWNT aggregates.

Preparation of Dye-Labeled $CS^{COV}$-SWNTs $CS^{COV}$-SWNT was labeled with Alexa Fluor 488 to estimate chloroplast localization efficiency of $CS^{COV}$-SWNT in plants. Alexa Fluor 488-NHS was mixed with $CS^{COV}$-SWNT (5 mg $mL^{-1}$) at a SWNT:dye ratio of 3:1 or 3:4 ratio (w/w) and this reaction mixture was subsequently stirred for 6 h at room temperature. The resulting Alexa Fluor 488-labeled $CS^{COV}$-SWNTs were dialyzed for 3 days against de-ionized water with dialysis membranes of 100 kDa MWCO to remove free dye molecules, and then centrifuged at 16,100 g for 1 h to remove SWNT aggregates.

Construction of pMBXS1120 and pBA-GFP-NLS Vectors

Vector pMBXS1120 (FIG. 10) is an 8.8 kb multi-functional plasmid containing genes encoding two visual markers (yellow fluorescence protein [YFP], and β-glucuronidase [GUS]) and one selectable marker (bar encoding phosphinothricin acetyltransferase imparting resistance to the herbicide bialaphos) for expression in plant chloroplasts. The three genes encoding these markers are arranged in one synthetic operon and are expressed from one promoter. The synthetic operon contains the following genetic elements: Prrn, the plastid ribosomal RNA operon promoter from *Nicotiana tabacum;* 5' UTR rbcL, 15 nucleotides of the 5' leader sequence of the gene encoding the large subunit of Rubisco from *Nicotiana tabacum*; bar, gene encoding bialoaphos resistance which has been codon optimized for expression in plants using preferred maize codons; 5' UTR T7g10, the 5' untranslated region of gene 10 of bacteriophage T7; YFP, a gene encoding the yellow fluorescent protein with a 239 amino acid sequence identical to the YFP protein at GenBank BAL45846. See, references 23 and 65-68.

The YFP gene has been codon optimized for expression in plants using preferred maize codons; rps19/rpl22 spacer, DNA homologous to nucleotides 86353 to 86390 of the tobacco plastome that contains part of the intergenic region between the rps19 and rpl22 genes; uidA, gene encoding the β-glucuronidase (GUS) protein which has been codon optimized for expression in plants using preferred maize codons; and 3'UTR psbA, the 3' untranslated region of the gene encoding the D1 protein of photosystem II. See, references 69-71. The synthetic operon is flanked on the left with a DNA fragment from *Panicum virgatum* containing the trnI gene (equivalent to bases 95,837 to 97,328 from the *P. virgatum* cultivar Kanlow chloroplast genome sequence at Gene ID HQ731441.1) and on the right with the trnA gene (right flank, equivalent to bases 97,329 to 98,268 from the *P. virgatum* cultivar Kanlow chloroplast genome sequence at Gene ID HQ731441.1). These flanking sequences can be used to insert the synthetic operon into the plastome of plants containing high homology to the *P. virgatum* trnI and trnA genes. The vector backbone of pMBXS1120 is derived from the pBluescript SK(−) cloning vector.

The GFP-NLS construct pBA-GFP-NLS is designed for nuclear transformation and has a length of 11291 nucleotides. In pBA-GFP-NLS, GFP-NLS is expressed under the cauliflower mosaic virus (CaMV) 35S promoter, and a SV40 NLS (nuclear localization signal) sequence was introduced at the C-terminal position of GFP. See, references 72-73.

Preparation of pDNA-SWNTs Conjugates

Chitosan-complexed SWNTs in MES buffer (20 mM MES, 10 mM $MgCl_2$, pH 5.7) were mixed with pDNA solution in different mass ratios. The mixture was then shaken at 500 rpm at room temperature for 30 minutes to allow for full condensation of the pDNA.

Hydrodynamic Radius Measurement of SWNTs

The NanoSight LM10 (NanoSight Ltd., Amesbury, United Kingdom) was used to analyze size distribution of SWNTs with a finely focused laser beam that is introduced to the nanoparticle suspension through a glass prism. Phase Analysis Light Scattering Zeta Potential Analyzer (PALS) was used to characterize the nanoparticle surface charge (NanoBrook ZetaPALS Potential Analyzer). The nanoparticle surface charge was averaged over 10 runs.

Atomic Force Microscopy of SWNTs

Silicon wafers ($Si/SiO_2$) were washed by acetone, isopropanol and water, and were blown dry by a nitrogen gun. Samples of SWNT were dropcasted onto a wafer. The substrates were allowed to dry for 3 h and were washed with water and blown dry by a nitrogen gun before imaging with Asylum Research MFP-3D AFM in tapping mode.

Release of pDNA from SWNTs

SWNT suspension was diluted with MMG buffer (0.4 M mannitol, 15 mM $MgCl_2$, 4 mM MES, pH 5.7) to make a concentration of 10 mg $L^{-1}$. Each sample was then allowed to form a complex with 0.5 μM dye-labeled single-stranded DNA, Cy3-$(GT)_{15}$ (Integrated DNA Technologies, Inc.), for 30 mins at room temperature while gently shaking. A control consisting of 0.5 μM Cy3-$(GT)_{15}$, deionized water, and MMG buffer was prepared. Sodium hydroxide (0.1 M) was incrementally added to both DNA-SWNT complex and the control to gradually increase pH, which was monitored by a pH meter (Thermo Scientific, Orian 2-Star pH meter). Fluorescence was measured at 574 nm using a microplate reader (Thermoscientific, Varioskan Flash) under the excitation at 540 nm. The percentage of free DNA was calculated based on calibration curve of free Cy3-$(GT)_{15}$ fluorescence intensity. All experiments were carried out in triplicates.

*Arabidopsis thaliana* Protoplast Isolation

Isolation of mesophyll protoplasts from leaves of *Arabidopsis thaliana* was performed as previously described by Yoo et al. with some modifications.[74] Briefly, well-expanded leaves from 3 week-old *Arabidopsis thaliana* plants were harvested before flowering. Thinly cut leaf strips were prepared using a fresh sharp razor blade without crushing the tissue. Leaf strips were transferred into the filtered enzyme solution (approximately 10 leaves in 10 ml of enzyme solution; enzyme solution contains 20 mM MES, 1.5% (w/v) cellulase R10 (Duchefa Biochemie), 0.4% (w/v) macerozyme R10 (Duchefa Biochemie), 0.4 M mannitol and 20 mM KCl with a pH of 5.7) and vacuum infiltrated for 30 min in the dark. The vacuum was then removed and digestion was continued without shaking in the dark for at least 3 h at room temperature. The enzyme/protoplast solution was diluted with an equal volume of MMG solution (0.4 M mannitol, 15 mM $MgCl_2$ and 4 mM MES with a pH of 5.7). A clean nylon mesh (75-μm) was soaked in 95% ethanol, rinsed with sterile water, and wetted with MMG solution before use. The enzyme solution containing protoplasts was then passed through the nylon mesh to remove undigested leaf material and the resulting flow-through was centrifuged (200 g) in a 30-ml round-bottomed tube for 2 min to pellet the protoplasts. The supernatant was removed and the protoplast pellet was re-suspended in MMG solution by gentle swirling. Protoplasts were allowed to settle at the bottom of the tube by gravity (15 min). The supernatant was removed and protoplasts were re-suspended in MMG solution to a concentration of about $10^5$ cells $mL^{-1}$.

Near-Infrared Microscopy

Isolated protoplasts were incubated with SWNT suspension or pDNA-SWNT complex (5 mg $L^{-1}$) in MMG buffer overnight at 4° C. Isolated protoplasts were located under bright field (×60 oil-immersion objective) and further visualized by observation of chloroplasts autofluorescence using a 900 nm band pass filter under a laser excitation of 785 nm (Invictus) with a modified Axiovision Zeiss microscope (×60 objective) attached to an OMV InGaAs linear array spectrometer (Princeton Instruments). The near infrared fluorescence of the SWNTs was monitored using a 900 nm long pass filter to minimize the influence of chloroplast autofluorescence.

Transient Expression in Protoplasts

100 μL of protoplast solution (approximately $10^4$ cells) was incubated with 3 mg $L^{-1}$ of pDNA-SWNT conjugates, or only pDNA (0.5 mg $L^{-1}$) for control samples, at room temperature for 3 h. The mixture was then centrifuged at 150 g for 3 mins to pellet the protoplasts before re-suspending the protoplasts in 1.5 mL of MMG buffer in a non-culture treated 12 well-plate (Corning). The protoplast suspension was incubated in the dark for 24 h at room temperature. A droplet of protoplast suspension was then transferred to a 35 mm poly-d-lysine coated glass bottom dish (Mattek Corporation) and fluorescence confocal microscopy was performed to visualize YFP expression.

Fluorescent Confocal Micrographs

Confocal images were taken in a Zeiss LSM 710 NLO microscope. Chitosan-complexed SWNT suspensions (1.5-5 mg $L^{-1}$) conjugated with pDNA in 20 mM MES-$MgCl_2$ buffer (pH 5.7) were infiltrated into the abaxial surface of the leaf lamina as attached to the living plants (mature wild-type arugula or watercress plant) by a localized infiltration method. The leaves were excised on the $1^{st}$, $2^{nd}$ and $3^{rd}$ day after infiltration, and leaf disc (5 mm in diameter) was prepared using a cork borer. The leaf disc was submerged in FM4-64 solution (10 μg $mL^{-1}$) to stain cell membranes after 5-10 tiny punctures were made on the lower surface of the leaf to improve penetration of the dye. After 3 h, the leaf disc was transferred to a microscope glass slide with a polydimethylsiloxne (PDMS) chamber filled with perfluorodecalin to obtain high image resolution at depth without affecting plant physiology. See, reference 75. The glass slide was sealed with a coverslip and imaged with a ×40 water immersion objective. The method of processing fluorescence micrographs to estimate transient gene expression efficiency published by Ueki et al., was followed with slight modifications. See, reference 76. The combined efficiency of chloroplast targeted gene delivery and transient expression was calculated by comparing the normalized mean intensity of the YFP fluorescence image with the normalized mean intensity of the chloroplast autofluorescence image, using fluorescence confocal micrographs. They were normalized to account for the different excitation power used to obtain each confocal micrograph. The mean pixel intensities from YFP or chloroplasts in confocal fluorescence micrographs were obtained using ImageJ software. The mean values of intensity obtained from five micrographs (354×354 μm) were used to estimate the combined efficiency of chloroplast targeted gene delivery and transient expression.

Colocalization efficiency between $CS^{COV}$-AF488-SWNT and chloroplasts was analyzed using the software ImageJ. Confocal images of *Nasturtium officinale* were split into $CS^{COV}$-AF488-SWNT and chloroplast autofluorescence channels and both channels were background-subtracted using the "Subtract background" function in ImageJ. The Manders' coefficients were then obtained using the COLOC2 analysis package to determine the colocalization/overlapping rate between the two channels.

*Agrobacterium*-Mediated Transformation

The pBA-GFP-NLS construct was transformed into *Agrobacterium* strain GV3101 using the freeze and thaw method. Cultured cells were harvested and resuspended in 10 mM MgCl$_2$ and 150 µM acetosyringone (Aldrich) and then kept at 25° C. for at least 3 hrs without shaking. *Agrobacterium* suspensions were infiltrated into leaves of 2-week old arugula plants with a needleless syringe. Leaf cells were analyzed using a LSM 510 laser scanning confocal microscope (Zeiss) 2-3 days after infiltration.

REFERENCES (EACH OF THE REFERENCES
DESCRIBED HEREIN ARE INCORPORATED
BY REFERENCE IN THEIR ENTIRETY)

1. Wang, Y. et al. Simultaneous editing of three homoeoalleles in hexaploid bread wheat confers heritable resistance to powdery mildew. *Nat. Biotechnol.* 32, 947-951 (2014).

2. Nyaboga, E., Tripathi, J. N., Manoharan, R. & Tripathi, L. *Agrobacterium*-mediated genetic transformation of yam (*Dioscorea rotundata*): an important tool for functional study of genes and crop improvement. *Front. Plant Sci.* 5, (2014).

3. Abdallah, N. A., Prakash, C. S. & McHughen, A. G. Genome editing for crop improvement: Challenges and opportunities. *GM crops & food* 6, 183-205 (2015).

4. Marsian, J. et al. Plant-made polio type 3 stabilized VLPs-A candidate synthetic polio vaccine. *Nat. Commun.* 8, (2017).

5. Sainsbury, F. & Lomonossoff, G. P. Extremely high-level and rapid transient protein production in plants without the use of viral replication. *Plant Physiol.* 148, 1212-8 (2008).

6. Lowe, K. et al. Morphogenic Regulators Baby boom and Wuschel Improve Monocot Transformation. *Plant Cell* 28, 1998-2015 (2016).

7. Li, J. F. et al. Multiplex and homologous recombination-mediated genome editing in *Arabidopsis* and *Nicotiana benthamiana* using guide RNA and Cas9. *Nature Biotechnology* 31, 688-691 (2013).

8. Yin, K., Gao, C. & Qiu, J.-L. Progress and prospects in plant genome editing. *Nat. Plants* 3, 17107 (2017).

9. Duke, S. O. Perspectives on transgenic, herbicide-resistant crops in the United States almost 20 years after introduction. *Pest Manag. Sci.* 71, 652-657 (2015).

10. Fischer, R., Stoger, E., Schillberg, S., Christou, P. & Twyman, R. M. Plant-based production of biopharmaceuticals. *Curr. Opin. Plant Biol.* 7, 152-158 (2004).

11. Juarez, P., Virdi, V., Depicker, A. & Orzaez, D. Biomanufacturing of protective antibodies and other therapeutics in edible plant tissues for oral applications. *Plant Biotechnol. J.* 14, 1791-1799 (2016).

12. Meyers, B., Zaltsman, A., Lacroix, B., Kozlovsky, S. V. & Krichevsky, A. Nuclear and plastid genetic engineering of plants: Comparison of opportunities and challenges. *Biotechnol. Adv.* 28, 747-756 (2010).

13. Skraly, F. A., Ambavaram, M. M. R., Peoples, O. & Snell, K. D. Metabolic engineering to increase crop yield: From concept to execution. *Plant Sci.* (2018). doi:10.1016/J.PLANTSCI.2018.03.011

14. Gilbert, N. Case studies: A hard look at GM crops. *Nature* 497, 24-26 (2013).

15. Fuentes, P., Armarego-Marriott, T. & Bock, R. Plastid transformation and its application in metabolic engineering. *Current Opinion in Biotechnology* 49, 10-15 (2018).

16. Jin, S. & Daniell, H. The Engineered Chloroplast Genome Just Got Smarter. *Trends in Plant Science* 20, 622-640 (2015).

17. Maliga, P. in *Genomics of chloroplasts and mitochondria, vol 35. Advances in Photosynthesis and Respiration* 393-414 (Springer, Dordrecht, 2012). doi:10.1007/978-94-007-2920-9_17.

18. Khan, M. S., Kanwal, B. & Nazir, S. Metabolic engineering of the chloroplast genome reveals that the yeast ArDH gene confers enhanced tolerance to salinity and drought in plants. Front. *Plant Sci.* 6, (2015).

19. Scott, S. E. & Wilkinson, M. J. Low probability of chloroplast movement from oilseed rape (*Brassica napus*) into wild *Brassica rapa*. *Nat. Biotechnol.* 17, 390-3292 (1999).

20. De Cosa, B., Moar, W., Lee, S. B., Miller, M. & Daniell, H. Overexpression of the Bt cry2Aa2 operon in chloroplasts leads to formation of insecticidal crystals. *Nat. Biotechnol.* 19, 71-74 (2001).

21. Staub, J. M. et al. High-yield production of a human therapeutic protein in tobacco chloroplasts. *Nat. Biotechnol.* 18, 333-338 (2000).

22. Fernández-San Millán, A., Mingo-Castel, A., Miller, M. & Daniell, H. A chloroplast transgenic approach to hyper-express and purify Human Serum Albumin, a protein highly susceptible to proteolytic degradation. *Plant Biotechnol. J* 1, 71-79 (2003).

23. Svab, Z. & Maliga, P. High-frequency plastid transformation in tobacco by selection for a chimeric aadA gene. *Proc. Natl. Acad. Sci.* 90, 913-917 (1993).

24. Golds, T., Maliga, P. & Koop, H. U. Stable plastid transformation in peg-treated protoplasts of *Nicotiana tabacum*. *Bio/Technology* 11, 95-97 (1993).

25. Cunningham, F. J., Goh, N. S., Demirer, G. S., Matos, J. L. & Landry, M. P. Nanoparticle-Mediated Delivery towards Advancing Plant Genetic Engineering. *Trends Biotechnol.* 0, (2018).

26. Rafsanjani, M. S. O., Alvari, A., Samim, M., Hejazi, M. A. & Abdin, M. Z. Application of novel nanotechnology strategies in plant biotransformation: a contemporary overview. *Recent Pat. Biotechnol.* 6, 69-79 (2012).

27. Ahmad, N., Michoux, F., Lossl, A. G. & Nixon, P. J. Challenges and perspectives in commercializing plastid transformation technology. *J. Exp. Bot.* 67, 5945-5960 (2016).

28. Rigano, M. M., Scotti, N. & Cardi, T. Unsolved problems in plastid transformation. *Bioengineered* 3, 329-33 (2012).

29. Whitehead, K. A. et al. Degradable lipid nanoparticles with predictable in vivo siRNA delivery activity. *Nat. Commun.* 5, (2014).

30. Wang, H. et al. Biocompatible Chitosan-Carbon Dot Hybrid Nanogels for NIR-Imaging-Guided Synergistic Photothermal-Chemo Therapy. *ACS Appl. Mater. Interfaces* 9, 18639-18649 (2017).

31. Deng, X. et al. Hyaluronic acid-chitosan nanoparticles for co-delivery of MiR-34a and doxorubicin in therapy against triple negative breast cancer. *Biomaterials* 35, 4333-4344 (2014).

32. Tripathi, D. K. et al. An overview on manufactured nanoparticles in plants: Uptake, translocation, accumulation and phytotoxicity. *Plant Physiology and Biochemistry* 110, 2-12 (2017).

33. Torney, F., Trewyn, B. G., Lin, V. S. Y. & Wang, K. Mesoporous silica nanoparticles deliver DNA and chemicals into plants. *Nat. Nanotechnol.* 2, 295-300 (2007).

34. Giraldo, J. P. et al. Plant nanobionics approach to augment photosynthesis and biochemical sensing. *Nat. Mater.* 13, 400-408 (2014).

35. Wong, M. H. et al. Lipid Exchange Envelope Penetration (LEEP) of Nanoparticles for Plant Engineering: A Universal Localization Mechanism. *Nano Lett.* 16, 1161-1172 (2016).

36. Lew, T. T. S. et al. Rational Design Principles for the Transport and Subcellular Distribution of Nanomaterials into Plant Protoplasts. *Small* 1802086 (2018). doi: 10.1002/smll.201802086

37. Serag, M. F., Kaji, N., Habuchi, S., Bianco, A. & Baba, Y. Nanobiotechnology meets plant cell biology: Carbon nanotubes as organelle targeting nanocarriers. *RSC Advances* 3, 4856-4862 (2013).

38. Li, Z., de Barros, A. L. B., Soares, D. C. F., Moss, S. N. & Alisaraie, L. Functionalized singlewalled carbon nanotubes: cellular uptake, biodistribution and applications in drug delivery. *Int. J. Pharm.* 524, (2017).

39. Liu, Q. et al. Carbon nanotubes as molecular transporters for walled plant cells. *Nano Lett.* 9, 1007-1010 (2009).

40. Wu, Y., Phillips, J. A., Liu, H., Yang, R. & Tan, W. Carbon Nanotubes Protect DNA Strands during Cellular Delivery. *ACS Nano* 2, 2023-2028 (2008).

41. Xiao-xiao He et al. Bioconjugated Nanoparticles for DNA Protection from Cleavage. (2003). doi:10.1021/JA034450D 42. Malerba, M. & Cerana, R. Recent Advances of Chitosan Applications in Plants. *Polymers (Basel)*. 10, 118 (2018).

43. Choudhary, R. C. et al. Cu-chitosan nanoparticle boost defense responses and plant growth in maize (*Zea mays* L.). *Sci. Rep.* 7, 9754 (2017).

44. Shearer, C. J. et al. Adsorption and Desorption of Single-Stranded DNA from Single-Walled Carbon Nanotubes. *Chem.-An Asian J.* 12, 1625-1634 (2017).

45. Yang, Y. et al. Binding efficacy and kinetics of chitosan with DNA duplex: The effects of deacetylation degree and nucleotide sequences. *Carbohydr. Polym.* 169, 451-457 (2017).

46. Jokerst, J. V, Lobovkina, T., Zare, R. N. & Gambhir, S. S. Nanoparticle PEGylation for imaging and therapy. *Nanomedicine (Lond)*. 6, 715-28 (2011).

47. Mathur, J. & Koncz, C. in *Arabidopsis Protocols* 267-276 (Humana Press, 1998). doi:10.1385/0-89603-391-0:267

48. Fettiplace, R., Andrews, D. M. & Haydon, D. A. Thickness, Composition and Structure of Some Lipid Bilayers and Natural Membranes. *J. Membr. Biol.* 5, 277-+(1971).

49. Zimmermann, U. & Neil, G. A. *Electromanipulation of cells*. (CRC press, 1996).

50. Heikkila, E. et al. Cationic Au Nanoparticle Binding with Plasma Membrane-like Lipid Bilayers: Potential Mechanism for Spontaneous Permeation to Cells Revealed by Atomistic Simulations. *J. Phys. Chem. C* 118, 11131-11141 (2014).

51. Wang, B., Zhang, L., Bae, S. C. & Granick, S. Nanoparticle-induced surface reconstruction of phospholipid membranes. *Proc. Natl. Acad. Sci.* 105, 18171-18175 (2008).

52. Kupiainen, M. et al. Free volume properties of sphingomyelin, DMPC, DPPC, and PLPC bilayers. *J. Comput. Theor. Nanosci.* 2, 401-413 (2005).

53. Nimesh, S., Thibault, M. M., Lavertu, M. & Buschmann, M. D. Enhanced gene delivery mediated by low molecular weight chitosan/DNA complexes: effect of pH and serum. *Mol. Biotechnol.* 46, 182-96 (2010).

54. Alberts, B. et al. *Molecular Biology of the Cell, 4th edition. Garland Science* (2002). doi:10.3389/fimmu.2015.00171

55. Mao, S., Sun, W. & Kissel, T. Chitosan-based formulations for delivery of DNA and siRNA. *Adv. Drug Deliv. Rev.* 62, 12-27 (2010).

56. Kruss, S. et al. Neurotransmitter detection using corona phase molecular recognition on fluorescent single-walled carbon nanotube sensors. *J. Am. Chem. Soc.* 136, 713-724 (2014).

57. Yang, R. et al. Carbon Nanotube-Quenched Fluorescent Oligonucleotides: Probes that Fluoresce upon Hybridization. *J Am. Chem. Soc.* 130, 8351-8358 (2008).

58. Lesney, M. S. Polycation-like behaviour of chitosan on suspension-culture derived protoplasts of slash pine. *Phytochemistry* 29, 1123-1125 (1990).

59. Kwak, S. Y. et al. A Nanobionic Light-Emitting Plant. *Nano Lett.* 17, 7951-7961 (2017).

60. Díaz, A. H. & Koop, H.-U. in 165-175 (Humana Press, Totowa, N.J., 2014). doi:10.1007/978-1-62703-995-6_9

61. Ruhlman, T. A. in 331-343 (Humana Press, Totowa, N.J., 2014). doi:10.1007/978-1-62703-995-6_21

62. Asensio, J. L., Ardá, A., Cañada, F. J. & Jiménez-Barbero, J. Carbohydrate-Aromatic Interactions. *Acc. Chem. Res.* 46, 946-954 (2013).

63. Svab, Z., Hajdukiewicz, P. & Maliga, P. Stable transformation of plastids in higher plants. *Proc. Natl. Acad. Sci.* 87, 8526-8530 (1990).

64. Rogalski, M., do Nascimento Vieira, L., Fraga, H. P. & Guerra, M. P. Plastid genomics in horticultural species: importance and applications for plant population genetics, evolution, and biotechnology. *Front. Plant Sci.* 6, (2015).

65. Suzuki, J. Y., Sriraman, P., Svab, Z. & Maliga, P. Unique architecture of the plastid ribosomal RNA operon promoter recognized by the multisubunit RNA polymerase in tobacco and other higher plants. *Plant Cell* 15, 195-205 (2003).

66. Bohmert-Tatarev, K., McAvoy, S., Daughtry, S., Peoples, O. P. & Snell, K. D. High Levels of Bioplastic Are Produced in Fertile Transplastomic Tobacco Plants Engineered with a Synthetic Operon for the Production of Polyhydroxybutyrate. *PLANT Physiol.* 155, 1690-1708 (2011).

67. Thompson, C. J. et al. Characterization of the herbicide-resistance gene bar from *Streptomyces hygroscopicus*. *EMBO J.* 6, 2519-23 (1987).

68. Kuroda, H. & Maliga, P. Sequences Downstream of the Translation Initiation Codon Are Important Determinants of Translation Efficiency in Chloroplasts. *PLANT Physiol.* 125, 430-436 (2001).

69. Herz, S., Füßl, M., Steiger, S. & Koop, H. U. Development of novel types of plastid transformation vectors and evaluation of factors controlling expression. *Transgenic Res.* 14, 969-982 (2005).

70. Jefferson, R. A., Kavanagh, T. A. & Bevan, M. W. GUS fusions: beta-glucuronidase as a sensitive and versatile gene fusion marker in higher plants. *EMBO J.* 6, 3901-7 (1987).

71. Staub, J. M. & Maliga, P. Accumulation of D1 polypeptide in tobacco plastids is regulated via the untranslated region of the psbA mRNA. *EMBO J.* 12, 601-606 (1993).

72. Benfey, P. N. & Chua, N. H. Regulated genes in transgenic plants. *Science* (80-.). 244, 174-181 (1989).

73. van der Krol, A. R. & Chua, N. H. The basic domain of plant B-ZIP proteins facilitates import of a reporter protein into plant nuclei. *Plant Cell* 3, 667-75 (1991).

74. Yoo, S. D., Cho, Y. H. & Sheen, J. *Arabidopsis* mesophyll protoplasts: A versatile cell system for transient gene expression analysis. *Nat. Protoc.* 2, 1565-1572 (2007).

75. Littlejohn, G. R., Gouveia, J. D., Edner, C., Smirnoff, N. & Love, J. Perfluorodecalin enhances in vivo confocal microscopy resolution of *Arabidopsis thaliana* mesophyll. *New Phytol.* 186, 1018-1025 (2010).

76. Ueki, S., Lacroix, B., Krichevsky, A., Lazarowitz, S. G. & Citovsky, V. Functional transient genetic transformation of *Arabidopsis* leaves by biolistic bombardment. *Nat. Protoc.* (2009). doi:10.1038/nprot.2008.217

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. A composition, comprising:
a chitosan-complexed single-walled carbon nanotube complexed with a gene cassette for delivery to a chloroplast, wherein the chitosan-complexed single-walled carbon nanotube comprises chitosan is covalently bonded to the single-walled carbon nanotube;
wherein the gene cassette comprises plasmid DNA;
wherein the gene cassette and the chitosan-complexed single-walled carbon nanotube are present in a ratio of 1:3 to 1:10 w/w of gene cassette to chitosan-complexed single-walled carbon nanotube; and
wherein the chitosan-complexed single-walled carbon nanotube complexed with the gene cassette has a zeta potential in the range of −35 to −30 mV or in the range of 30 to 35 mV.

2. The composition of claim 1, wherein the chitosan is deacetylated.

3. The composition of claim 1, wherein the polysaccharide chitosan is pegylated.

4. The composition of claim 1, wherein the gene cassette includes a zinc finger nuclease, a TALEN vector or a CRISPR/Cas vector.

5. A method of delivering genetic material to a plant chloroplast comprising:
contacting a plant with the composition of claim 1.

6. The method of claim 5, wherein the plant is a watercress plant, a tobacco plant, a spinach plant or isolated *Arabidopsis thaliana* mesophyll protoplast.

7. The method of claim 5, further comprising releasing the genetic material in the interior of a chloroplast.

8. The composition of claim 1, wherein a threshold zeta potential is determined by Equation 1:

$$\xi^* = \pm\left(\frac{\varepsilon_M + \varepsilon_W}{\varepsilon_W}\right)\left(\frac{d}{a}\right)e^{\kappa(d-a)}\sqrt{\frac{(\Gamma - a\gamma_0 + 4a\Delta\Delta H\rho_n)L}{2a\varepsilon_0\varepsilon_M\left(1 - \frac{\varepsilon_M}{\varepsilon_W}\right)}} \quad \text{(Equation 1)}$$

wherein:
$\varepsilon_M$, a relative permittivity of a double lipid bilayers of the chloroplast, is about 2.2;
$\varepsilon_W$, a relative permittivity of a medium of the chloroplast, is about 80;
$\varepsilon_0$, a dielectric permittivity of vacuum, is about $8.854 \times 10^{-12}$ F/m;
"d" is an effective charge radius of the composition;
"a" is a radius of the composition;
$\kappa^{-1}$ is a Debye-Huckle screening length of the composition;
$\Gamma$, a pore line tension of the chloroplast, is about $10^{-12}$ N;
$\gamma_0$, a resting membrane tension of the chloroplast, is about 0.6 mN/m;
$\Delta\Delta H$, a change in free energy due to the lipid of the chloroplast binding on the composition, is about 0.05 $k_b T$;
$\rho_n$, a lipid density on the composition, is about $10^{18}$; and
L, a thickness of the double lipid bilayers of the chloroplast, is about $1.1 \times 10^{-10}$ m,
wherein the radius of the composition is in the range of 104-190 nm.

9. The composition of claim 1, wherein the zeta potential is about −30 m V or about 30 m V.

10. The composition of claim 1, wherein the gene cassette and the chitosan-complexed single-walled carbon nanotube are present in a ratio of 1:3 to 1:6 w/w of gene cassette to chitosan-complexed single-walled carbon nanotube.

11. A composition, comprising:
a chitosan-complexed single-walled carbon nanotube complexed with a gene cassette for delivery to a chloroplast in a plant,
wherein the chitosan-complexed single-walled carbon nanotube comprises chitosan is covalently bonded to the single-walled carbon nanotube;
wherein the gene cassette comprises plasmid DNA;
wherein the gene cassette and the chitosan-complexed single-walled carbon nanotube are present in a ratio of 1:3 to 1:10 w/w of gene cassette to chitosan-complexed single-walled carbon nanotube; and
wherein the chitosan-complexed single-walled carbon nanotube complexed with the gene cassette has a zeta potential in the range of −35 to −30 mV or in the range of 30 to 35 mV; and
wherein the plant is a watercress plant, a tobacco plant, a spinach plant or isolated *Arabidopsis thaliana* mesophyll protoplast.

12. The composition of claim 1, wherein the chloroplast is in a plant, and the composition is in contact with the plant.

13. The composition of claim 11, wherein the composition is in contact with the plant.

* * * * *